United States Patent
Schiltz et al.

(10) Patent No.: US 10,093,668 B2
(45) Date of Patent: Oct. 9, 2018

(54) SUBSTITUTED AROMATIC N-HETEROCYCLIC COMPOUNDS AS INHIBITORS OF MITOGEN-ACTIVATED PROTEIN KINASE INTERACTING KINASE 1 (MNK1) AND 2 (MNK2)

(71) Applicant: Northwestern University, Evanson, IL (US)

(72) Inventors: Gary E. Schiltz, Naperville, IL (US); Rama K. Mishra, Chicago, IL (US); Leonidas C. Platanias, Glencoe, IL (US); Javier Izquierdo-Ferrer, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/337,332

(22) Filed: Oct. 28, 2016

(65) Prior Publication Data

US 2017/0121326 A1   May 4, 2017

Related U.S. Application Data

(60) Provisional application No. 62/247,504, filed on Oct. 28, 2015.

(51) Int. Cl.
| | |
|---|---|
| *C07D 403/04* | (2006.01) |
| *C07D 471/04* | (2006.01) |
| *C07D 401/14* | (2006.01) |
| *C07D 403/14* | (2006.01) |
| *C07D 405/14* | (2006.01) |
| *C07D 413/14* | (2006.01) |

(52) U.S. Cl.
CPC ......... *C07D 471/04* (2013.01); *C07D 401/14* (2013.01); *C07D 403/04* (2013.01); *C07D 403/14* (2013.01); *C07D 405/14* (2013.01); *C07D 413/14* (2013.01)

(58) Field of Classification Search
CPC .......................... C07D 403/04; A61K 31/506
USPC .......................................... 544/317; 514/274
See application file for complete search history.

(56) References Cited

U.S. PATENT DOCUMENTS

| 7,790,756 B2 * | 9/2010 | Flynn ................... C07D 401/12 514/341 |
| 2009/0170095 A1 | 7/2009 | Steuernagel et al. |
| 2010/0022538 A1 * | 1/2010 | Boebel ................. C07D 239/47 514/235.8 |

FOREIGN PATENT DOCUMENTS

| WO | 2013174780 A1 | 11/2013 |
| WO | 2014088519 A1 | 6/2014 |

OTHER PUBLICATIONS

Mu et al., Understanding DP receptor antagonism using a CoMSIA approach, BioorganiC & Medicinal Chemistry Letters, 21 (1), pp. 66-75, 2011.*
Zegzouti, et al., "ADP-Glo: A Bioluminescent and Homogeneous ADP Monitoring Assay for Kinases", Assay and Drug Development Technologies, vol. 7, No. 6, Dec. 2009, pp. 560-572.
International Search Report and Written Opinion for PCT/US2016/059347 dated Feb. 16, 2017.
International Preliminary Report on Patentability for PCT/US2016/059347 dated May 1, 2018.

* cited by examiner

*Primary Examiner* — Deepak R Rao
(74) *Attorney, Agent, or Firm* — Andrus Intellectual Property Law, LLP

(57) ABSTRACT

Disclosed are substituted aromatic N-heterocyclic compounds. The disclosed compounds typically exhibit kinase inhibition activity, for example, and inhibit Mnk1 kinase and/or Mnk2 kinase. The disclosed compounds may be used in pharmaceutical compositions and methods for treating diseases or disorders associated with Mnk1 kinase activity and/or Mnk2 kinase activity, such as cancers, diabetes, autism, and fragile X syndrome.

13 Claims, No Drawings

SUBSTITUTED AROMATIC N-HETEROCYCLIC COMPOUNDS AS INHIBITORS OF MITOGEN-ACTIVATED PROTEIN KINASE INTERACTING KINASE 1 (MNK1) AND 2 (MNK2)

CROSS-REFERENCED TO RELATED PATENT APPLICATIONS

This application claims the benefit of priority under 35 U.S.C. § 119(e) to U.S. Provisional Application No. 62/247,504, filed on Oct. 28, 2015, the content of which is incorporated herein by reference in its entirety.

BACKGROUND

The field of the invention relates to compounds that inhibit mitogen-activated protein kinase interacting kinases 1 and/or 2 (Mnk1 and/or Mnk2). In particular, the field of the invention relates to substituted N-heterocyclic aromatic-based compounds as inhibitors of Mnk1 and/or Mnk2 for the treatment for the treatment of diseases and disorders associated with Mnk1 and/or Mnk2, including cell proliferative diseases or disorders (e.g., cancers such as AML), diabetes, autism, and fragile X syndrome.

While treatment options have improved in recent years, cancer remains the second leading cause of death in the United States. Many cancers lack effective treatments and have poor long-term prognoses. In particular, acute myeloid leukemia (AML) is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for only ~1% of cancer deaths in the United States, the incidence of AML is expected to increase as the U.S. population ages. As an acute leukemia, AML progresses rapidly and is typically fatal within weeks or months if left untreated.

Here, as part of an effort to discover and evaluate new small molecules that have the potential for treating human cancer, in particular hematological malignancies such as AML, we have identified a series of so-called substituted N-heterocyclic aromatic-based compounds that display potent in vitro cytotoxicity against AML cells, involving targeting an enzyme in the cell called Mnk. Compound analogs have been synthesized and tested to generate robust structure-activity relationships based on multiple sites of diversification. Lead compounds possess excellent profiles as potential therapeutics based on a variety of physiochemical properties. These new compounds therefore hold promise as new potential treatments for cancers such as AML and other proliferative diseases.

Because the compounds disclosed herein are shown to be inhibitors of Mnk, these compounds may be useful for treating other diseases and disorders associated with Mnk-activity. Mnk kinase phosphorylates eIF4E, whose activity has been implicated in disorders such as diabetes (U.S. Published Application No. 20090170095 A1), autism (Nature 493, 371-377), and fragile X syndrome (Nature Neuroscience 16, 1530-1536 (2013)).

SUMMARY

Disclosed are substituted aromatic N-heterocyclic compounds. The disclosed compounds typically exhibit kinase inhibition activity, for example, of Mnk1 kinase and/or Mnk2 kinase. The disclosed compounds may be used in pharmaceutical compositions and methods for treating diseases or disorders associated with Mnk1 kinase activity and/or Mnk2 kinase activity.

The disclosed compounds may be described as having a Formula I:

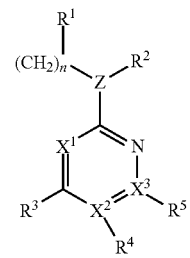

wherein:

$X^1$, $X^2$, and $X^3$ are the same or different and are C or N, and preferably no more than one of $X^1$, $X^2$, and $X^3$ is N;

Z is N or O;

n=0, 1, 2, or 3;

$R^1$ is hydrogen, alkyl, alkyoxyl, hydroxyl, hydroxyalkyl, carboxyl, carboxyalkylester, cycloalkyl (e.g., cyclobutyl, cyclopentyl, and cyclohexyl) optionally substituted at one or more positions with hydroxyl or alkoxyl, amino optionally substituted with alkyl (e.g., methylamino or dimethylamino), amido optionally substituted with phenyl or substituted phenyl (e.g., 3,5-ditrifluoromethylphenyl), thioamido, phenyl optionally substituted at one or more positions with halo (e.g., fluoro) or amido, pyridinyl (e.g., N-pyridinyl, 2-pyridinyl, 3-pyridinyl, or 4-pyridinyl), pyrrolidinyl (e.g., N-pyrrolidinyl, 2-pyrrolidinyl, or 3-pyrrolidinyl), tetrahydropyranyl (e.g., 2-tetrahydropyranyl, 3-tetrahydropyranyl, or 4-tetrahydropyranyl), tetrahydrofuranyl (e.g., 2-tetrahydrofuranyl or 3-tetrahydrofuranyl), oxetanyl (e.g., oxetan-2-yl or oxetan-3-yl), pyrrolidonyl (e.g., N-2-pyrrolidonyl), piperidinyl (e.g., N-piperidinyl, 2-piperidinyl, 3-piperidinyl, or 4-piperidinyl), piperazinyl optionally substituted with alkyl (e.g., N-piperazinyl, N-(1-methylpiperazinyl, or piperazin-2-yl), morpholinyl (e.g., N-morpholinyl), imidazolyl (e.g., 1H-imidazol-1-yl, 1H-imidazol-2-yl, or 1H-imidazol-4-yl) optionally substituted at one or more positions with alkyl (e.g., methyl or ethyl such as N-methylimidazole or N-ethylimidazole), pyrazolyl (e.g., 1H-pyrazol-1-yl, 1H-pyrazol-3-yl, or 1H-pyrazol-4-yl), benzyamidyl (e.g., 4-benzamidyl), N-methylbenzamid-4-yl, benzoyl (e.g., benzo-4-yl), benzoylpiperazine (e.g., 4-benzoylpiperazine), N-phenylformamidyl, indolyl (e.g., N-indolyl, 1H-indol-2-yl, or 1H-indol-3-yl), or R1 has a structure selected from

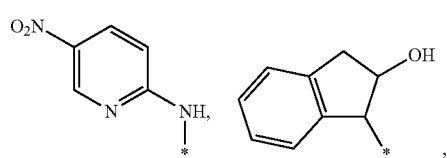

-continued

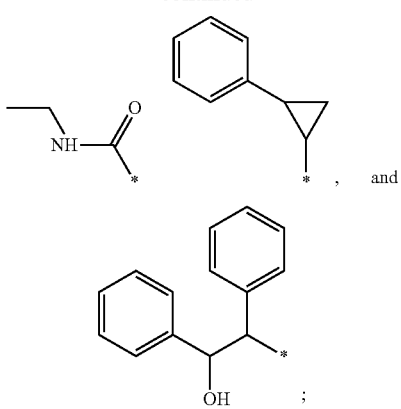

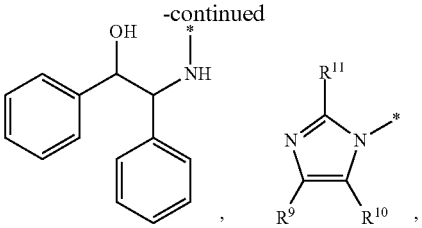

R² is hydrogen or R² and R¹ together form one 5-membered ring, one 6-membered ring, or one 7-membered ring which ring is optionally aromatic and saturated or unsaturated and optionally substituted with one or more heteroatoms (e.g., N-pyrrolidinyl, or caprolactam (e.g., caprolactam-3-yl)) or R² and R¹ together form two fused rings which may be 5-membered rings or 6-membered rings which rings are optionally aromatic and saturated or unsaturated and optionally substituted with one or more heteroatoms (e.g., N-benzimidazole, or 1H-indazo-1-yl);

R³ has a structure selected from

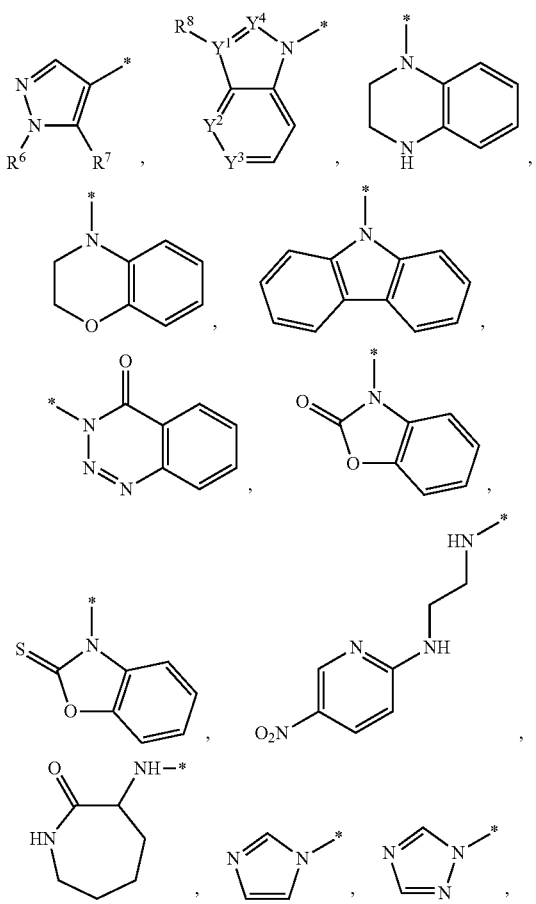

or R³ is aminoalkylindolyl (e.g., aminoethylindo-3-yl), aminoalkylpyridinyl (e.g., aminoethylpyridin-3-yl or aminoethylpyridin-4-yl), aminoalkylpyrrolidonyl (e.g., aminopropyl-N-pyrrolidonyl), or aminohydroxyalkyl (e.g., amino-2-propanol);

$R_4$ is hydrogen, alkyl (e.g., methyl), haloalkyl (e.g., trifluoromethyl), halo, (e.g., fluoro, chloro, or bromo), alkoxy (e.g., methoxy), cyano, amino, hydroxyl, carboxyl, or carboxy alkyl ester;

$R^5$ is hydrogen, amino, carboxyl, carboxy alkyl ester, carboxy amido, carboxy alkyl amido (e.g., N-cyclopropylformamide), or N-benzimidazole;

$R^6$ is hydrogen, alkyl (e.g., methyl, ethyl, or propyl), phenyl optionally substituted at one or more positions with alkyoxy (e.g., 2-methoxy or 3-methoxy) or halo (e.g., 2-chloro or 3-chloro), tetrahydropuranyl (e.g., tetrahydropuran-4-yl), alkylmorpholinyl (e.g., ethyl-N-morpholinyl), and benzyl;

$Y^1$ is C or N;
$Y^2$ is C or N;
$Y^3$ is C or N;
$Y^4$ is C or N;
$R^7$ is hydrogen, or alkyl (e.g., methyl);
$R^8$ is hydrogen or phenyl optionally substituted at one or more positions with alkyoxy (e.g., 2-methoxy or 3-methyoxy); and
$R^9$, $R^{10}$, and $R^{11}$ are the same or different and are hydrogen, alkyl, or phenyl.

In particular, the disclosed compounds may have a formula selected from:

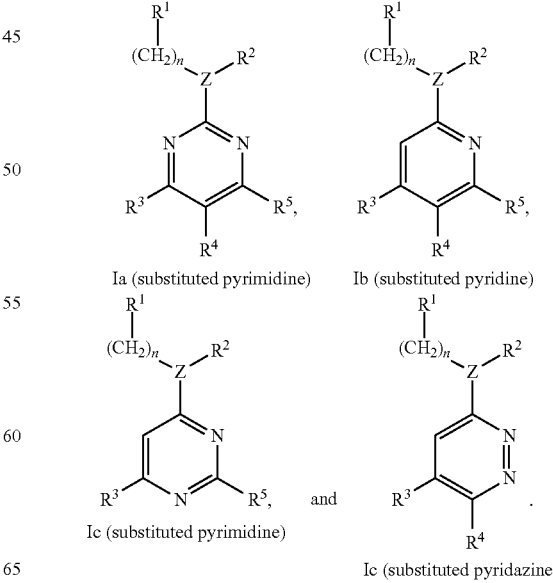

Typically in the disclosed compounds having Formula I, either Z is a nitrogen atom and/or $R^3$ is attached to the pyrimidine core via a nitrogen atom. In embodiments in which the compounds have a Formula Ia (i.e., substituted pyrimidine compounds) and either Z is a nitrogen atom and/or $R^3$ is attached to the pyrimidine core via a nitrogen atom, the disclosed compounds may be referred to as "aminopyrimidine-based compounds."

Also disclosed are pharmaceutical compositions that comprise the disclosed compounds together with a carrier, diluent, or excipient. The pharmaceutical compositions may comprise an effective amount of the compounds (or salts, esters, amides, or solvates thereof) for treating and/or preventing a disease, disorder, or condition associated with Mnk1 and/or Mnk2 activity. Diseases, disorders, and conditions associated with Mnk1 and/or Mnk2 activity may include but are not limited to cell proliferation diseases disorders (e.g. such as cancer), diabetes, autism, and fragile X syndrome.

Also disclosed are methods of treating diseases or disorders associated with Mnk1 and/or Mnk2 activity. The methods typically include administering the disclosed compounds to a patient in need thereof, for example, where the compounds are formulated as a pharmaceutical composition and administered to a patient having a disease or disorder associated with Mnk1 and/or Mnk2 activity or suspected of having a disease or disorder associated with Mnk1 and/or Mnk2 activity. Diseases and disorders associated with Mnk1 and/or Mnk2 activity may include cell proliferative diseases or disorders (e.g., cancers), diabetes, autism, and/or fragile X syndrome. Cancers treated by the disclosed methods may include, but are not limited to leukemia (e.g., acute myeloid leukemia), multiple myeloma, non-small cell lung cancer, colon cancer, cancer of the central nervous system, melanoma, ovarian cancer, renal cancer, prostate cancer, and breast cancer.

DETAILED DESCRIPTION

The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The term "alkyl" as contemplated herein includes a straight-chain or branched alkyl radical in all of its isomeric forms. Alkyl groups may include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$ alkenyl, $C_2$-$C_{10}$ alkenyl, and $C_2$-$C_6$ alkenyl, respectively. Exemplary alkenyl groups include vinyl, allyl, butenyl, pentenyl, hexenyl, butadienyl, pentadienyl, hexadienyl, and the like.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$ alkynyl, $C_2$-$C_{10}$ alkynyl, and $C_2$-$C_6$ alkynyl, respectively. Exemplary alkynyl groups include ethynyl, prop-1-yn-1-yl, and but-1-yn-1-yl.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, (e.g., as "$C_{4-8}$cycloalkyl") derived from a cycloalkane. Exemplary cycloalkyl groups include, but are not limited to, cyclohexanes, cyclopentanes, cyclobutanes and cyclopropanes. Cycloalkyl groups may be optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. Cycloalkyl groups can be fused to other cycloalkyl, aryl, or heterocyclyl groups. In certain embodiments, the cycloalkyl group is not substituted (i.e., unsubstituted).

The term "haloalkyl" refers to an alkyl group that is substituted at one or more positions with at least one halogen. Haloalkyls may include, —$CH_2F$, —$CHF_2$, —$CF_3$, —$CH_2CF_3$, —$CF_2CF_3$, $CH_3Cl$, $CH_2Cl_2$, and the like.

The term "heteroalkyl" as used herein refers to an "alkyl" group in which at least one carbon atom has been replaced with a heteroatom (e.g., an O, N, or S atom). In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). One type of heteroalkyl group is an "alkoxyl" group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted (i.e., unsubstituted).

The term "cycloalkenyl" as used herein refers to a monovalent unsaturated cyclic, bicyclic, or bridged cyclic (e.g., adamantyl) hydrocarbon group of 3-12, 3-8, 4-8, or 4-6 carbons containing one carbon-carbon double bond, referred to herein, e.g., as "C4-$_8$cycloalkenyl," derived from a cycloalkane. Exemplary cycloalkenyl groups include, but are not limited to, cyclohexenes, cyclopentenes, and cyclobutenes. Unless specified otherwise, cycloalkenyl groups are optionally substituted at one or more ring positions with, for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkenyl group is not substituted (i.e., unsubstituted).

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "bicyclic carbocyclyl that is partially unsaturated" refers to a bicyclic carbocyclic group containing at least one double bond between ring atoms and at least one ring in the bicyclic carbocyclic group is not aromatic.

The terms "heterocyclyl" and "heterocyclic group" are art-recognized and refer to saturated, partially unsaturated, or aromatic 3-membered ring structures to 10-membered ring structures, alternatively 3-membered ring structures to 7-membered ring structures, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$ heterocyclyl group refers to a saturated or partially unsaturated 3-membered ring structure to a 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a C$_3$heterocyclyl is aziridinyl. Heterocycles may also be mono-, bi-, or other multicyclic ring systems including a spirocyclic ring system where at least one ring contains a ring heteroatom. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "bicyclic heterocyclyl" refers to a heterocyclyl group that contains two rings that are fused together. In certain embodiments, the bicyclic heterocyclyl is an carbocyclic ring fused to partially unsaturated heterocyclic ring, that together form a bicyclic ring structure having 8-10 ring atoms (e.g., where there are 1, 2, 3, or 4 heteroatoms selected from the group consisting of nitrogen, oxygen, and sulfur).

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The terms "amine" and "amino" are art-recognized and refer to both unsubstituted and substituted amines, e.g., a moiety represented by the general formula —N($R^1$)($R^2$), wherein $R^1$ and $R^2$ each independently represent hydrogen, alkyl, cycloalkyl, heterocyclyl, alkenyl, aryl, aralkyl, or —$(CH_2)_m$—$R^3$; or $R^1$ and $R^2$, taken together with the N atom to which they are attached complete a heterocycle having from 4 to 8 atoms in the ring structure; $R^3$ represents an aryl, a cycloalkyl, a cycloalkenyl, a heterocycle or a poly cycle; and m is zero or an integer in the range of 1 to 8. In certain embodiments, $R^1$ and $R^2$ each independently represent hydrogen, alkyl, alkenyl, or —$(CH_2)_m$—$R^3$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R^3$, where m and $R^3$ are described above.

The term "carbamate" as used herein refers to a radical of the form —$R^1OC(O)N(R^2)$—, —$R^1OC(O)N(R^2)R^3$—, or —$OC(O)NR^2R^3$, wherein $R^1$, $R^2$ and $R^3$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of $R^1$, $R^2$, and $R^3$ are independently aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R^1$, $R^2$, or $R^3$. The amide also may be cyclic, for example $R^1$ and $R^2$, $R^2$ and $R^3$, or $R^1$ and $R^3$ may be joined to form a 3- to 12-membered ring, such as a 3- to 10-membered ring or a 5- to 6-membered ring.

As used herein, an asterisk "*" is used to designate the point of attachment for any radical group or substituent group.

As used herein, a "patient" may be interchangeable with "subject" or "individual" and means an animal, which may be a human or non-human animal, in need of treatment.

A "patient in need of treatment" may include a patient having a disease, disorder, or condition that is responsive to therapy with an inhibitor of Mnk1 kinase and/or Mnk2 kinase. For example, a "patient in need of treatment" may include a patient having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer). A "patient in need of treatment" also may include a patient having diabetes, autism, and/or fragile X syndrome.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The formulae of the compounds disclosed herein should be interpreted as encompassing all possible stereoisomers, enantiomers, or epimers of the disclosed compounds unless the formulae indicates a specific stereoisomer, enantiomer, or epimer. The formulae of the compounds disclosed herein should be interpreted as encompassing salts, esters, amides, or solvates thereof of the compounds.

The disclosed compounds may be effective in inhibiting cell proliferation of cancer cells. For example, the disclosed compound may be effective in inhibiting cell proliferation of one or more types of cancer cells including: leukemia cells, such as CCRF-CEM, HL-60(TB), MOLT-4, RPMI-8226 and SR; multiple myeloma cells, such as MM.1S cells; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D.

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an $IC_{50}$ of less than about 10 µM, 5 µM, 1 µM, or 0.5 µM in the selected assay.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

Pyridine-based compounds have been disclosed as inhibitors of Src kinase. (See U.S. Pat. No. 6,498,165, the content of which is incorporated herein by reference in its entirety). The disclosed compounds preferably inhibit the kinase activity of Mnk1, otherwise referred to as mitogen-activated protein kinase interacting kinase 1. (See Oyarzabal et al., J. Med. Chem. 2010 Sep. 23; 53(18):6618-28, the content of which is incorporated herein by reference in its entirety). Inhibition of Mnk kinase activity results in suppressive effects on acute myeloid leukemia. (See Altman et al., Blood 2013 May 2; 121(18):3675-81, the content of which is incorporated herein by reference in its entirety). Mnk kinase also phosphorylates eIF4E, which has also been implicated in disorders such as diabetes (U.S. Patent No. 20090170095 A1), autism (Nature 493, 371-377), and fragile X (Nature Neuroscience 16, 1530-1536 (2013)). In some embodiments, the disclosed compounds inhibit the kinase activity of Mnk1 and/or Mnk2 and have an $IC_{50}$ of less than about 100 µM, 10 µM, 1 µM, 0.5 µM, 0.1 µM, 0.05 µM, 0.01 µM, 0.005 or 0.001 µM.

Substituted Aromatic N-Heterocyclic Compounds as Inhibitors of Mitogen-Activated Protein Kinase Interacting Kinases (MNK) 1 and 2

Disclosed are substituted aromatic N-heterocyclic compounds which have been shown to inhibit mitogen-activated protein kinase interacting kinases 1 and 2 (MNK1 and MNK2). The disclosed compounds may be described as having a Formula I:

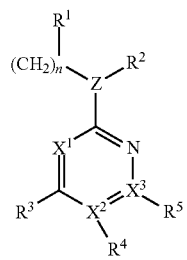

wherein:
$X^1$, $X^2$, and $X^3$ are the same or different and are C or N, and preferably no more than one of $X^1$, $X^2$, and $X^3$ is N;
Z is N or O;
n=0, 1, 2, or 3;
$R^1$ is hydrogen, alkyl, alkyoxyl, hydroxyl, hydroxyalkyl, carboxyl, carboxyalkylester, cycloalkyl (e.g., cyclobutyl, cyclopentyl, and cyclohexyl) optionally substituted at one or more positions with hydroxyl or alkoxyl, amino optionally substituted with alkyl (e.g., methylamino or dimethylamino), amido optionally substituted with phenyl or substituted phenyl (e.g., 3,5-ditrifluoromethylphenyl), thioamido, phenyl optionally substituted at one or more positions with halo (e.g., fluoro) or amido, pyridinyl (e.g., N-pyridinyl, 2-pyridinyl, 3-pyridinyl, or 4-pyridinyl), pyrrolidinyl (e.g., N-pyrrolidinyl, 2-pyrrolidinyl, or 3-pyrrolidinyl), tetrahydropyranyl (e.g., 2-tetrahydropyranyl, 3-tetrahydropyranyl, or 4-tetrahydropyranyl), tetrahydrofuranyl (e.g., 2-tetrahydrofuranyl or 3-tetrahydrofuranyl), oxetanyl (e.g., oxetan-2-yl or oxetan-3-yl), pyrrolidonyl (e.g., N-2-pyrrolidonyl), piperidinyl (e.g., N-piperidinyl, 2-piperidinyl, 3-piperidinyl, or 4-piperidinyl), piperazinyl optionally substituted with alkyl (e.g., N-piperazinyl, N-(1-methylpiperazinyl, or piperazin-2-yl), morpholinyl (e.g., N-morpholinyl), imidazolyl (e.g., 1H-imidazol-1-yl, 1H-imidazol-2-yl, or 1H-imidazol-4-yl) optionally substituted at one or more positions with alkyl (e.g., methyl or ethyl such as N-methylimidazole or N-ethylimidazole), pyrazolyl (e.g., 1H-pyrazol-1-yl, 1H-pyrazol-3-yl, or 1H-pyrazol-4-yl), benzyamidyl (e.g., 4-benzamidyl), N-methylbenzamid-4-yl, benzoyl (e.g., benzo-4-yl), benzoylpiperazine (e.g., 4-benzoylpiperazine), N-phenylformamidyl, indolyl (e.g., N-indolyl, 1H-indol-2-yl, or 1H-indol-3-yl), or R1 has a structure selected from

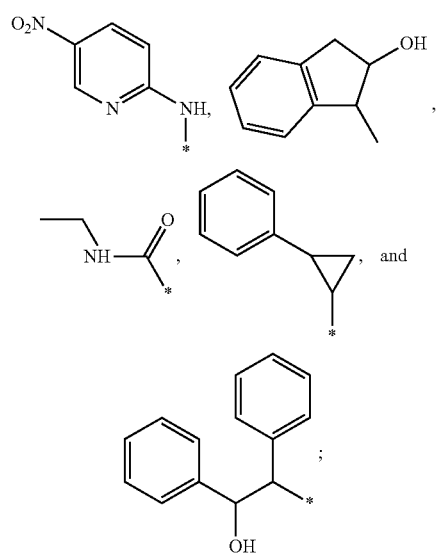

$R^2$ is hydrogen or $R^2$ and $R^1$ together form one 5-membered ring, one 6-membered ring, or one 7-membered ring which ring is optionally aromatic and saturated or unsaturated and optionally substituted with one or more heteroatoms (e.g., N-pyrrolidinyl, or caprolactam (e.g., caprolactam-3-yl)) or $R^2$ and $R^1$ together form two fused rings which may be 5-membered rings or 6-membered rings which rings are optionally aromatic and saturated or unsaturated and optionally substituted with one or more heteroatoms (e.g., N-benzimidazole, or 1H-indazo-1-yl);

$R^3$ has a structure selected from

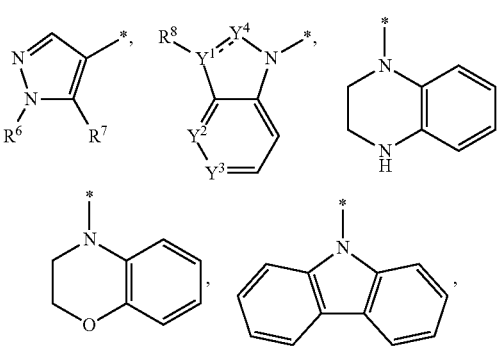

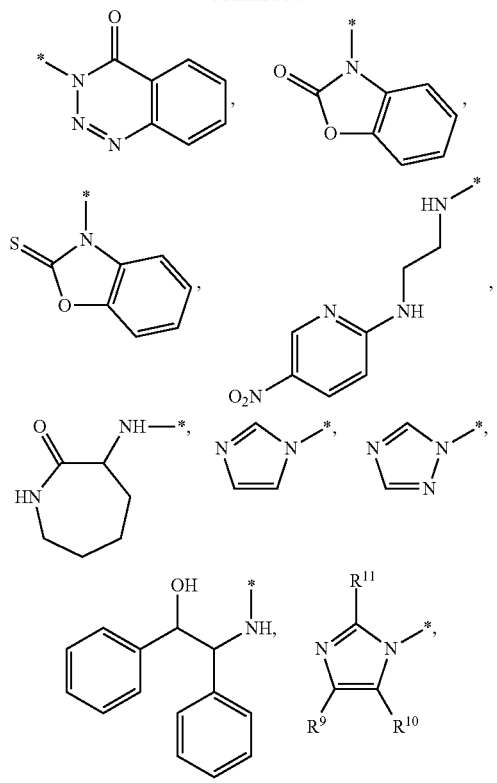

or R³ is aminoalkylindolyl (e.g., aminoethylindo-3-yl), aminoalkylpyridinyl (e.g., aminoethylpyridin-3-yl or aminoethylpyridin-4-yl), aminoalkylpyrrolidonyl (e.g., aminopropyl-N-pyrrolidonyl), or aminohydroxyalkyl (e.g., amino-2-propanol);

$R_4$ is hydrogen, alkyl (e.g., methyl), haloalkyl (e.g., trifluoromethyl), halo, (e.g., fluoro, chloro, or bromo), alkoxy (e.g., methoxy), cyano, amino, hydroxyl, carboxyl, or carboxy alkyl ester;

$R^5$ is hydrogen, amino, carboxyl, carboxy alkyl ester, carboxy amido, carboxy alkyl amido (e.g., N-cyclopropyl-formamide), or N-benzimidazole;

$R^6$ is hydrogen, alkyl (e.g., methyl, ethyl, or propyl), phenyl optionally substituted at one or more positions with alkyoxy (e.g., 2-methoxy or 3-methoxy) or halo (e.g., 2-chloro or 3-chloro), tetrahydropuranyl (e.g., tetrahydropuran-4-yl), alkylmorpholinyl (e.g., ethyl-N-morpholinyl), and benzyl;

$Y^1$ is C or N;

$Y^2$ is C or N;

$Y^3$ is C or N;

$Y^4$ is C or N;

$R^7$ is hydrogen, or alkyl (e.g., methyl);

$R^8$ is hydrogen or phenyl optionally substituted at one or more positions with alkyoxy (e.g., 2-methoxy or 3-methyoxy); and $R^9$, $R^{10}$, and $R^{11}$ are the same or different and are hydrogen, alkyl, or phenyl.

In some embodiments of the disclosed, the disclosed compounds may have a formula selected from:

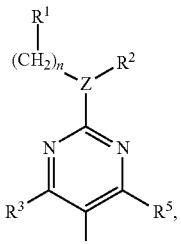
Ia (substituted pyrimidine)

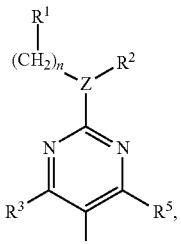
Ib (substituted pyridine)

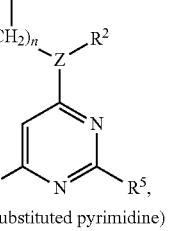
Ic (substituted pyrimidine) and

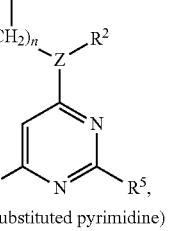
Id (substituted pyridazine)

Typically in the disclosed compounds having Formula I, either Z is a nitrogen atom and/or R³ is attached to the pyrimidine core via a nitrogen atom. In embodiments in which the compounds have a Formula Ia (i.e., substituted pyrimidine compounds) and either Z is a nitrogen atom and/or R³ is attached to the pyrimidine core via a nitrogen atom, the disclosed compounds may be referred to as "aminopyrimidine-based compounds."

In some embodiments, the disclosed compounds may have a formula selected from selected from Formula II and III:

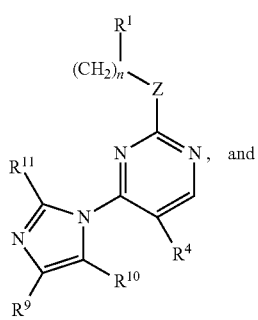

II

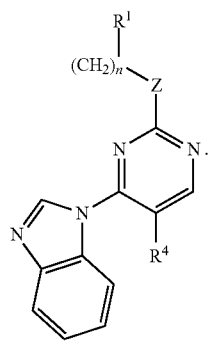

III

In further embodiments of compounds having Formula II, the compounds disclosed herein may have Formula IIa or IIb as follows:

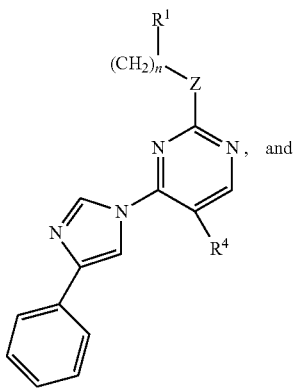

IIa

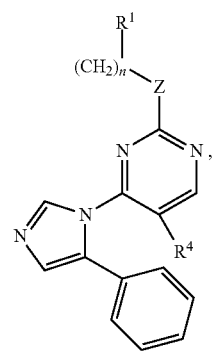

IIb wherein R⁴ optionally is halo or cyano.

In further embodiments of compounds having Formula III, the compounds disclosed herein may have Formula IIIa as follows:

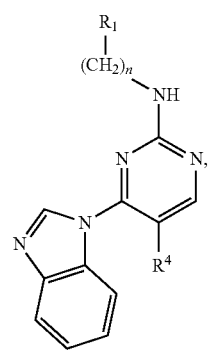

IIIa wherein optionally R¹ is pyridin-3-yl or pyridin-4-yl, and/or R⁴ is halo or cyano.

The disclosed compounds may be utilized to prepare pharmaceutical compositions. The disclosed pharmaceutical compositions may include an effective amount of any of the disclosed compounds together with a carrier, excipient, or diluent.

The disclosed compounds and pharmaceutical compositions may be administered in methods of treatment. In some embodiments, the disclosed methods include methods of treating a disease or disorder associated with Mnk1 activity and/or Mnk2 activity in a patient in need thereof, the method comprising administering an effective amount of any of the disclosed compounds or a pharmaceutical composition comprising an effective amount of any of the disclosed compounds.

The disclosed compounds preferably inhibit the activity of Mnk1 and/or Mnk2. As such, the disclosed methods of treatment including methods of treating a disease or disorder that is associated with Mnk1 activity and/or Mnk2 activity. Suitable diseases and disorders for the disclosed methods of treatment may include cancer or a cell proliferative disorder, including hematological malignancies such as acute myeloid leukemia (AML). Other suitable diseases and disorders for the disclosed methods of treatment may include diabetes, autism, and fragile X syndrome.

Formulations

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

EXAMPLES

The following Examples are illustrative and are not intended to limit the scope of the claimed subject matter.

There is an urgent need for the development of innovative new approaches for the treatment of acute myeloid leukemia (AML). We have identified a unique methodology to kill AML cells, involving targeting of an enzyme in the cells called Mnk. We previously have shown that blocking Mnk results in potent antileukemic effects against AML precursors in bone marrow from patients with AML and in AML mouse models. We also were able to demonstrate that targeting Mnk potentiates the antileukemic effects of chemotherapeutic agents used in the treatment of AML. Using a molecular modeling based high-throughput screen, we have identified a new series of compounds that act as Mnk inhibitors. We have optimized this series into a set of potent, novel lead compounds that inhibit Mnk activity.

Chemistry

General Experimental

All chemical reagents were obtained from commercial suppliers and used without further purification unless otherwise stated. Anhydrous solvents were purchased from Sigma-Aldrich, and dried over 3 Å molecular sieves when necessary. DCM and THF were purified by passage through a bed of activated alumina. Normal-phase flash column chromatography was performed using Biotage KP-Sil 50 μm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light or iodine vapor. Liquid chromatography/mass spectrometry (LCMS) was performed on a Waters Acquity-H UPLC system with a 2.1 mm×50 mm, 1.7 μm, reversed phase BEH C18 column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). Proton ($^1$H) and carbon ($^{13}$C) NMR spectra were recorded on a Bruker Avance III w/ direct cryoprobe spectrometer. Chemical shifts were reported in ppm (δ) and were referenced using residual non-deuterated solvent as an internal standard. The chemical shifts for $^1$H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. In some cases, overlapping signals occurred in the $^{13}$C NMR spectra.

As described below, the compounds of Table 1-4 were synthesized per one of synthetic routes A, B, C, D, or E.

Scheme 1.

Route A

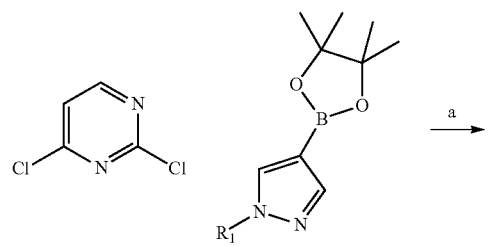

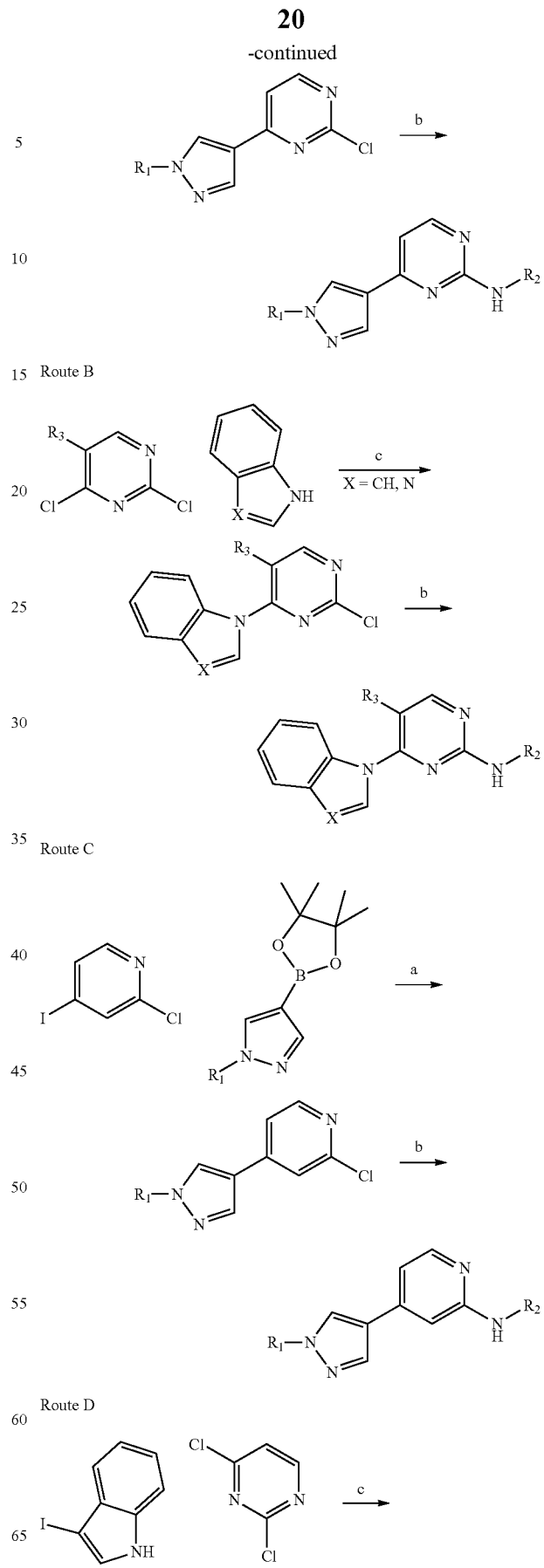

Route B

Route C

Route D

21
-continued

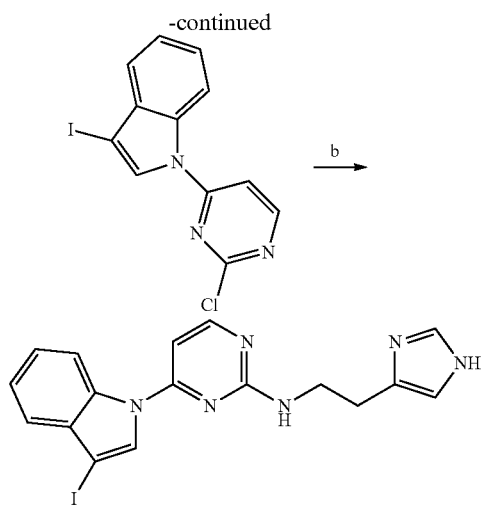

Route E

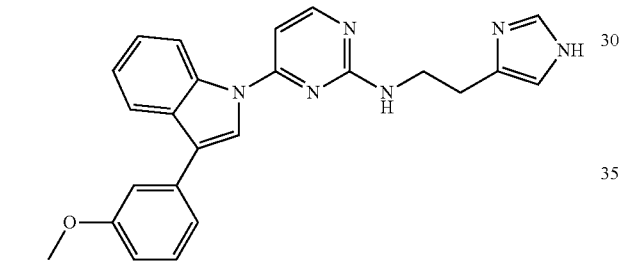

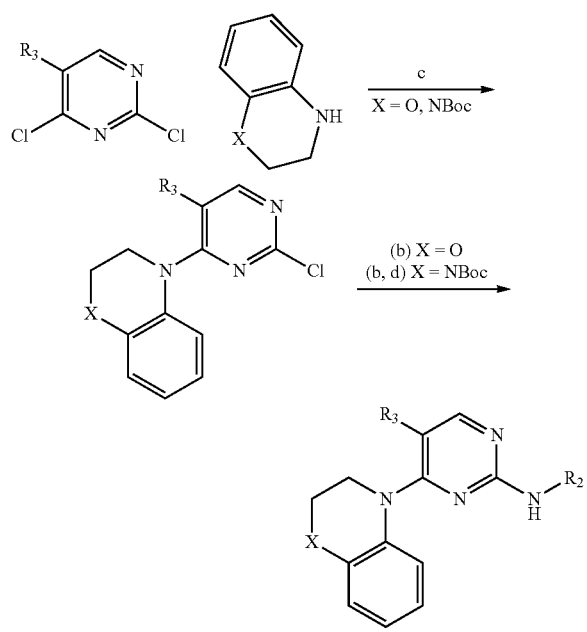

(a) Pd(PPh3)4, toluene, EtOH, Na2CO3 (aq); (b) TEA, CH3CN; (c) NaH, DMF; (d) TFA, DCM

22

Example of Compound Synthesis Using Route A

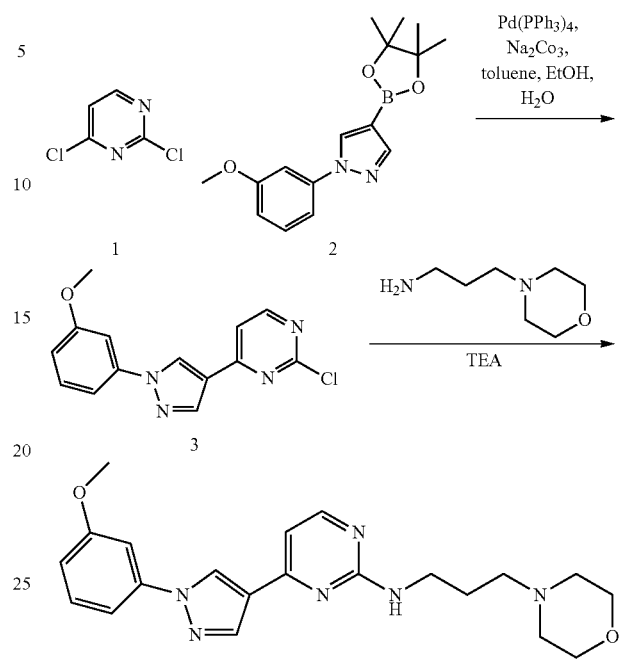

NUCC-77154

2-chloro-4-(1-(3-methoxyphenyl)-1H-pyrazol-4-yl)pyrimidine (3)

A mixture of 2,4-dichloropyrimidine (0.133 g, 0.893 mmol), 1-(3-methoxyphenyl)-4-(4,4,5,5-tetramethyl-1,3,2-dioxaborolan-2-yl)-1H-pyrazole (0.268 g, 0.893 mmol), Pd(Ph3P)4 (0.103 g, 0.089 mmol) and Na2CO3 (1.339 ml, 2.68 mmol) in EtOH (0.9 ml) and toluene (2.7 ml) was heated at 150 C using a microwave reactor for 15 min. H2O and EtOAc were added and layers separated. The organic layer was dried over anhydrous Na2SO4 and evaporated to give a crude residue which was purified by silica-gel chromatography (0-50% EtOAc in Hex) to yield the product as a yellow solid. MS (ESI): mass calcd. for $C_{14}H_{11}ClN_4O$, 286.72; m/z found, 287.1 [M+H]+.

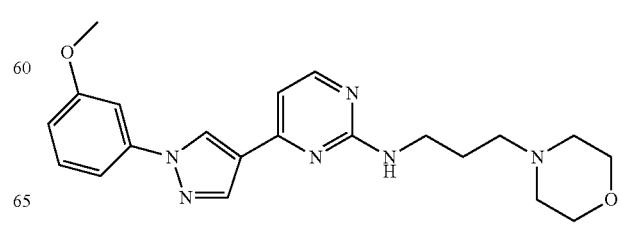

4-(1-(3-methoxyphenyl)-1H-pyrazol-4-yl)-N-(3-morpholinopropyl)pyrimidin-2-amine (NUCC-77154)

A mixture of 2-chloro-4-(1-(3-methoxyphenyl)-1H-pyrazol-4-yl)pyrimidine (12 mg, 0.042 mmol), 3-morpholinopropan-1-amine (0.031 ml, 0.209 mmol) and TEA (0.020 ml, 0.146 mmol) in Acetonitrile (0.25 ml) and DMSO (0.25 ml) was heated at 150 C using a microwave reactor for 30 min. H2O and EtOAc were added and layers separated. The organic layer was dried over anhydrous Na2SO4 and evaporated to give a crude residue which was purified by silica-gel chromatography (0-10% MeOH in DCM) to yield the product as a semi-solid. MS (ESI): mass calcd. for $C_{21}H_{26}N_6O_2$, 394.47; m/z found, 395.35 [M+H]+; $^1$H NMR (500 MHz, CDCl$_3$) δ 1.86 (t, J=6.41 Hz, 2H) 2.52 (br. s., 5H) 3.57 (q, J=6.21 Hz, 2H) 3.77 (br. s., 4H) 3.90 (s, 3H) 5.72 (br. s., 1H) 6.75 (d, J=5.19 Hz, 1H) 6.86-6.93 (m, 1H) 7.30 (dd, J=7.93, 1.22 Hz, 1H) 7.34-7.41 (m, 2H) 8.17 (s, 1H) 8.27 (d, J=5.19 Hz, 1H) 8.46 (s, 1H); 13C NMR (126 MHz, CDCl3) δ 25.87, 29.72, 40.37, 53.73, 55.59, 57.12, 66.91, 105.31, 105.99, 111.34, 113.03, 126.44, 130.32, 139.85, 140.88, 158.26, 158.96, 160.61, 162.65.

Example of Compound Synthesis Using Route B

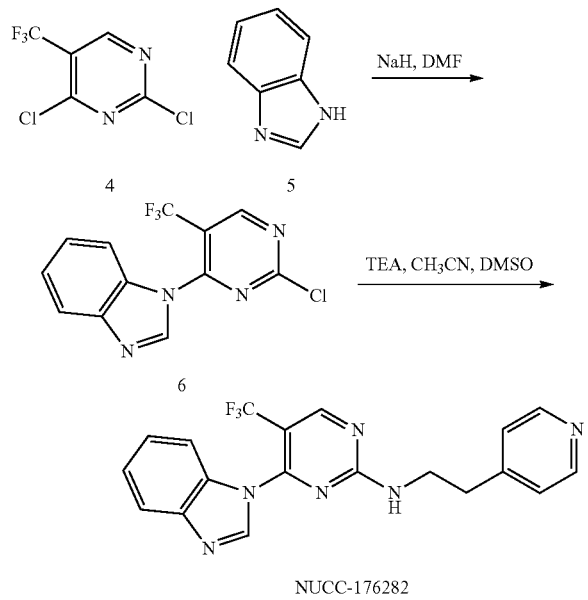

4-(1H-benzo[d]imidazol-1-yl)-N-(2-(pyridin-4-yl)ethyl)-5-(trifluoromethyl)pyrimidin-2-amine (NUCC-176282)

Into a 0.5-2 mL microwave vial with a stirrer, 1-(2-chloro-5-(trifluoromethyl)pyrimidin-4-yl)-1H-benzo[d]imidazole (55 mg, 0.184 mmol), acetonitrile (0.4 ml), DMSO (0.2 ml), Et3N (0.051 ml, 0.368 mmol), and 2-(pyridin-4-yl)ethanamine (0.077 µl, 0.645 mmol) were added. Then, the vial was sealed heated in the microwave for 35 min at 150 C. Then, the greenish suspension was diluted with DCM introduced and concentrated under reduced pressure overnight. The crude was crystallized with AcOEt:DCM and a small amount of MeOH. The product that precipitated was recrystallized again to afford NUCC-176282. MS (ESI): mass calcd. for $C_{19}H_{15}F_3N_6$, 384.36; m/z found, 385.34 [M+H]+; $^1$H NMR (500 MHz, CDCl$_3$) δ 3.14 (t, J=7.1 Hz, 2H), 4.03 (m, 2H), 5.53-5.62 (m, 1H), 7.28 (m, 2H), 7.37-7.44 (m, 2H), 7.84-7.90 (m, 1H), 8.51 (m, 2H), 8.58-8.63 (m, 2H), 9.05 (s, 1H).

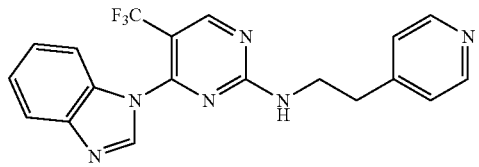 [SMILES: FC(F)(F)c1cnc(NCCc2ccncc2)nc1-n1cnc2ccccc21]

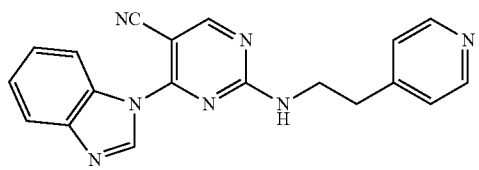 [SMILES: N#Cc1cnc(NCCc2ccncc2)nc1-n1cnc2ccccc21]

NUCC-176343

MS (ESI): mass calcd. for $C_{19}H_{15}N_7$, 341.37; m/z found, 342.24 [M+H]+; 3.10 (t, J=7.3 Hz, 2H), 3.96-4.05 (m, 2H), 5.88 (br. s.), 7.21-7.24 (m, 2H), 7.39-7.43 (m, 2H), 7.84-7.89 (m, 1H), 8.46-8.49 (m, 1H), 8.54 (s, 1H), 8.59-8.62 (m, 2H), 9.02 (s).

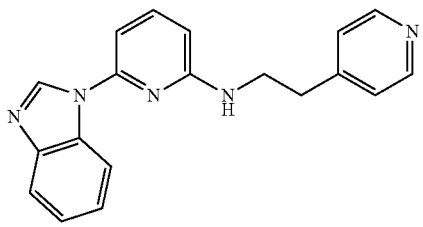 [SMILES: c1cc(NCCc2ccncc2)nc(-n2cnc3ccccc32)c1]

NUCC-0196235

MS (ESI): mass calcd. for $C_{19}H_{17}N_5$, 315.37; m/z found, 316.2 [M+H]+; 1H NMR (500 MHz, CHLOROFORM-d) δ 8.52-8.60 (m, 3H), 8.03-8.11 (m, 1H), 7.85-7.92 (m, 1H), 7.62 (t, J=7.63 Hz, 1H), 7.38 (td, J=1.34, 4.96 Hz, 2H), 7.16-7.23 (m, 2H), 6.87 (d, J=7.63 Hz, 1H), 6.38 (d, J=7.93 Hz, 1H), 4.69-4.76 (m, 1H), 3.72-3.83 (m, 2H), 3.03 (t, J=7.0 Hz, 2H).

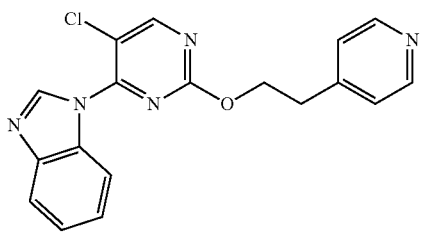 [SMILES: Clc1cnc(OCCc2ccncc2)nc1-n1cnc2ccccc21]

NUCC-0196254

MS (ESI): mass calcd. for $C_{18}H_{14}ClN_5O$, 351.79; m/z found, 352.1 [M+H]+; 1H NMR (500 MHz, CHLOROFORM-d) δ 8.97 (s, 1H), 8.61 (d, J=5.80 Hz, 2H), 8.50 (s, 1H), 8.45-8.48 (m, 1H), 7.84-7.89 (m, 1H), 7.42 (dquin, J=1.37, 7.29 Hz, 2H), 7.31-7.35 (m, 2H), 4.85 (t, J=6.41 Hz, 2H), 3.27 (t, J=6.56 Hz, 2H).

Example of Compound Synthesis Using Route E

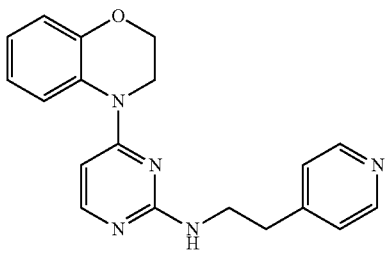 [SMILES: c1ccc2c(c1)OCCN2c1ccnc(NCCc2ccncc2)n1]

NUCC-0176230

MS (ESI): mass calcd. for $C_{19}H_{19}N_5O$, 333.39; m/z found, 334.4 [M+H]+; 1H NMR (500 MHz, Methanol-$d_4$) δ 8.40 (d, J=5.19 Hz, 2H), 7.83 (d, J=6.10 Hz, 1H), 7.41 (dd, J=1.37, 8.09 Hz, 1H), 7.32 (d, J=5.49 Hz, 2H), 7.05 (dd, J=1.37, 7.17 Hz, 1H), 6.84-6.96 (m, 2H), 6.49 (d, J=6.10 Hz, 1H), 4.20-4.29 (m, 2H), 4.11-4.16 (m, 2H), 3.68 (t, J=7.02 Hz, 2H), 2.96 (t, J=7.02 Hz, 2H). 13C NMR (126 MHz, Methanol-$d_4$) δ 161.08, 150.36, 148.40, 147.62, 125.66, 124.82, 123.21, 119.55, 117.33, 65.89, 41.66, 41.12, 34.81.

Mnk1 and Mnk2 Inhibition

The synthesized compounds then were tested for inhibition of the kinase activity ($IC_{50}$) of Mnk1 and/or Mnk2 using the ADP monitoring assay for kinases described in Zegzouti, H.; Zdanovskaia, M.; Hsiao, K.; Goueli, S. A., ADP-Glo: A Bioluminescent and homogeneous ADP monitoring assay for kinases. *Assay and drug development technologies* 2009, 7 (6), 560-72, the content of which is incorporated herein by reference. Results are presented in Tables 1 and 2.

Cellular Inhibition of Mnk1

To evaluate inhibition of Mnk1 in cells, we utilized a flow cytometry-based assay based on activation of eIF-4E, the downstream target of Mnk1. The assay utilizes flow cytometry to quantitatively measure the amount of eIF-4E that is phosphorylated at residue Ser209 in cell lysate from U937 or MV4-11 cell lines. Cells grown in the presence of serum were treated with vehicle or test compounds across a range of concentrations. Levels of phospho-eIF-4E were measured and $IC_{50}$ values were determined by logistic regression to quantify the potency of each compound. Results are presented in Tables 3 and 4.

Cell Viability Assay

To measure the ability of the new Mnk1/2 inhibitors to kill cancer cells in vitro, U937 or MV4-11 cells were incubated with different concentrations of test compounds and analyzed for apoptosis and cell viability at 5 and 24 hours post-treatment. Viability (assessed by ATP levels with Cell-Titer-Glo, Promega) and apoptosis (assessed by Annexin V staining) were graphed and logistic regression was used to determine inhibitor concentration that induced 50% of the maximal effect ($EC_{50}$). Decreased viability was always accompanied by a commensurate increase in apoptosis, thus confirming the viability results. Results are presented in Tables 3 and 4.

TABLE 1

| | | Mnk1 | Mnk2 | Synthetic |
|---|---|---|---|---|
| Structure | Molecule Name | IC$_{50}$ | IC$_{50}$ | Route |
| | NUCC-0054131 | 6 μM | 2.1 μM | A |
| | NUCC-0054132 | 9 μM | | A |
| | NUCC-0054133 | 7 μM | 1.8 μM | A |

TABLE 1-continued
Mnk1 and Mnk2 Inhibition.
| Structure | Molecule Name | Mnk1 IC$_{50}$ | Mnk2 IC$_{50}$ | Synthetic Route |
| --- | --- | --- | --- | --- |
| 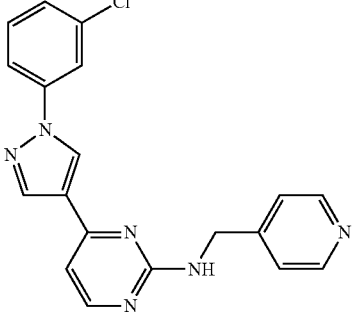 | NUCC-0054134 | 6 μM | | A |
| 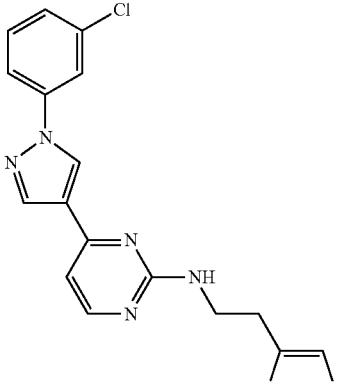 | NUCC-0054135 | 6 μM | | A |
| 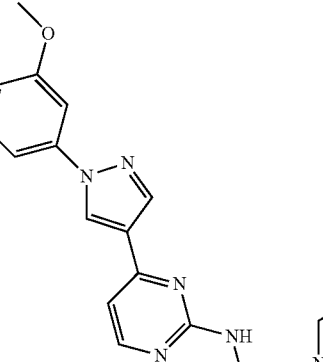 | NUCC-0054136 | 10 μM | | A |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 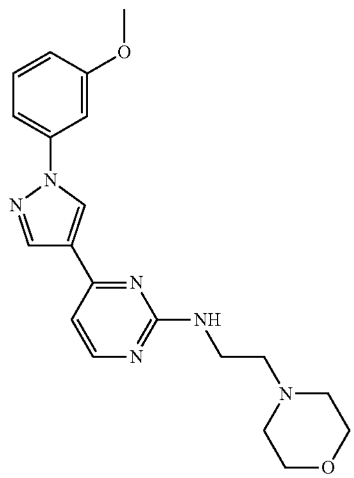 [SMILES: COc1cccc(-n2cc(-c3ccnc(NCCN4CCOCC4)n3)cn2)c1] | NUCC-0054138 | 12 μM | | A |
| 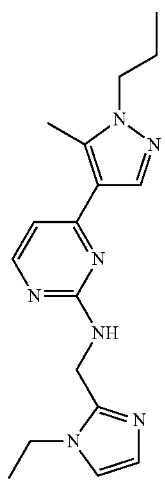 [SMILES: CCCn1ncc(-c2ccnc(NCc3nccn3CC)n2)c1C] | NUCC-0054147 | 6 μM | 16 μM | A |
| 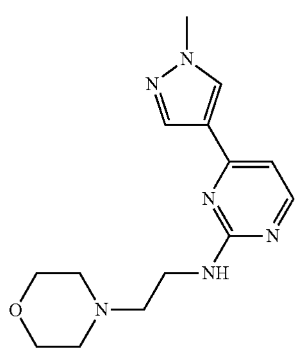 [SMILES: Cn1cc(-c2ccnc(NCCN3CCOCC3)n2)cn1] | NUCC-0060894 | 4 μM | | A |
| 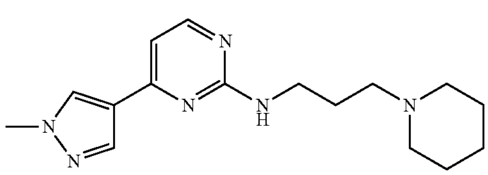 [SMILES: Cn1cc(-c2ccnc(NCCCN3CCCCC3)n2)cn1] | NUCC-0060895 | 5 μM | | A |

TABLE 1-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 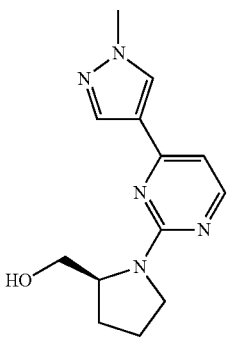 [SMILES: Cn1cc(-c2ccnc(N3CCC[C@H]3CO)n2)cn1] | NUCC-0060896 | 3 μM | 3.4 μM | A |
| 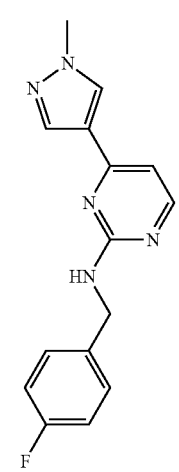 [SMILES: Cn1cc(-c2ccnc(NCc3ccc(F)cc3)n2)cn1] | NUCC-0060897 | 9 μM | | A |
| 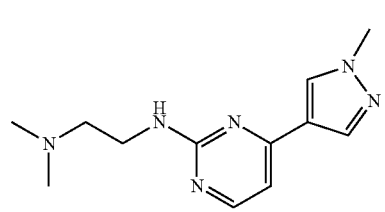 [SMILES: CN(C)CCNc1nccc(-c2cnn(C)c2)n1] | NUCC-0060898 | 5 μM | | A |
| 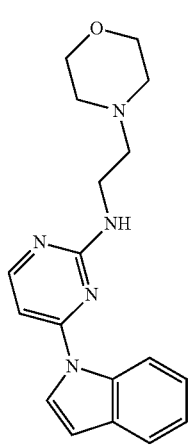 [SMILES: c1ccc2c(c1)ccn2-c1ccnc(NCCN2CCOCC2)n1] | NUCC-0060953 | 9 μM | | B |

TABLE 1-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 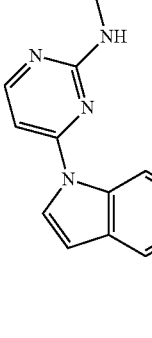 | NUCC-0060954 | 4 μM | 4.0 μM | B |
| 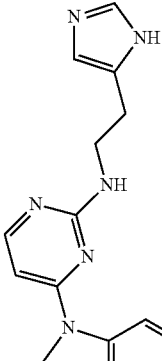 | NUCC-0060955 | 16 μM | 5.0 μM | B |
| 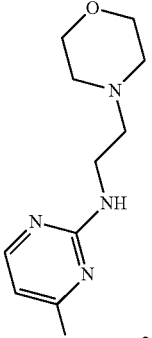 | NUCC-0060956 | 1 μM | | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 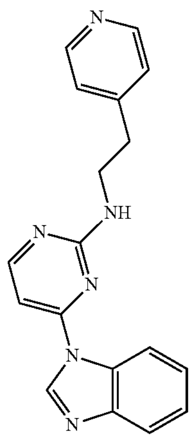 [SMILES: c1ccc2c(c1)ncn2-c1ccnc(NCCc2ccncc2)n1] | NUCC-0060957 | 0.16 µM | 0.045 µM | B |
| 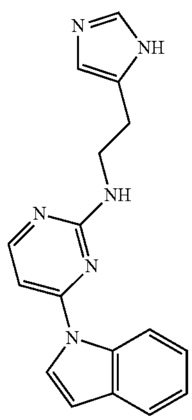 [SMILES: c1ccc2c(c1)ccn2-c1ccnc(NCCc2cnc[nH]2)n1] | NUCC-0060958 | 0.9 µM | 0.095 µM | B |
| 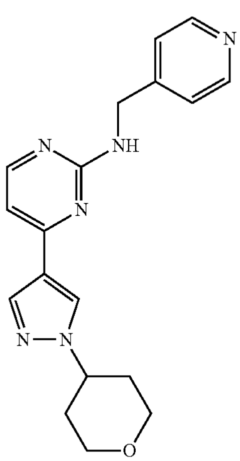 [SMILES: c1cc(CNc2nccc(-c3cnn(C4CCOCC4)c3)n2)ccn1] | NUCC-0060959 | 90 µM |  | A |

TABLE 1-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 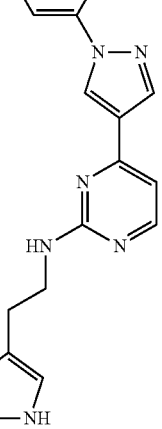 | NUCC-0060965 | 30 μM | | A |
| 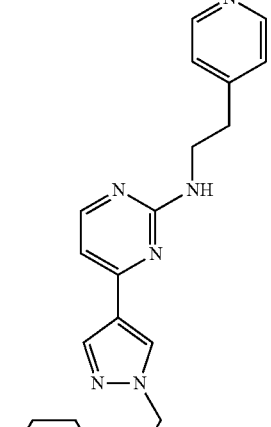 | NUCC-0060970 | 70 μM | | A |
| 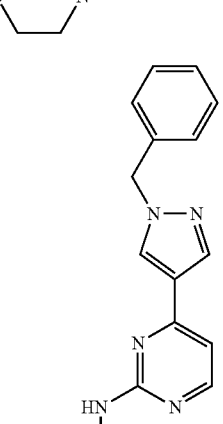 | NUCC-0060971 | 19 μM | | A |

TABLE 1-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 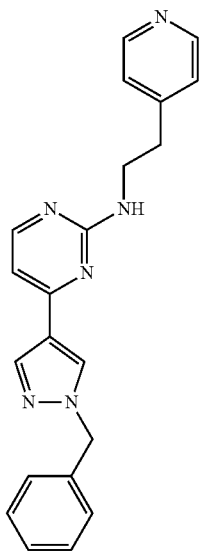 [SMILES: c1ccc(Cn2cc(-c3ccnc(NCCc4ccncc4)n3)cn2)cc1] | NUCC-0060972 | 19 μM | 2.5 μM | A |
| 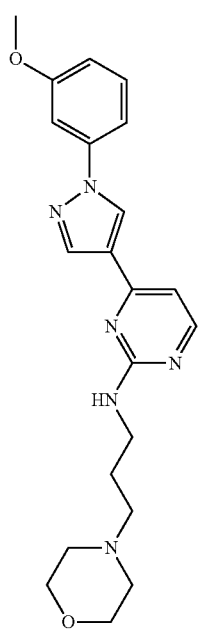 [SMILES: COc1cccc(-n2cc(-c3ccnc(NCCCN4CCOCC4)n3)cn2)c1] | NUCC-0077154 | 28 μM | | A |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 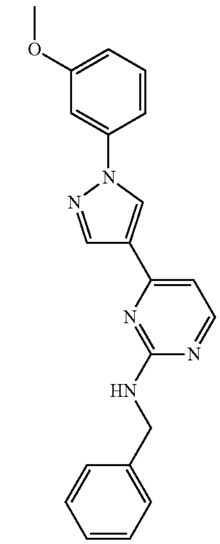 [SMILES: COc1cccc(-n2cc(-c3ccnc(NCc4ccccc4)n3)cn2)c1] | NUCC-0077155 | 21 μM | | A |
| 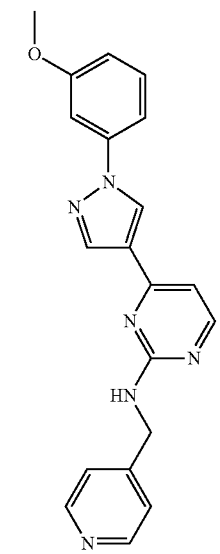 [SMILES: COc1cccc(-n2cc(-c3ccnc(NCc4ccncc4)n3)cn2)c1] | NUCC-0077163 | 8 μM | | A |
| 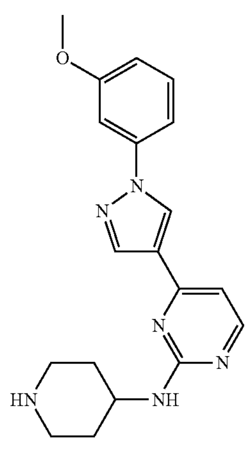 [SMILES: COc1cccc(-n2cc(-c3ccnc(NC4CCNCC4)n3)cn2)c1] | NUCC-0077164 | 6 μM | | A |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 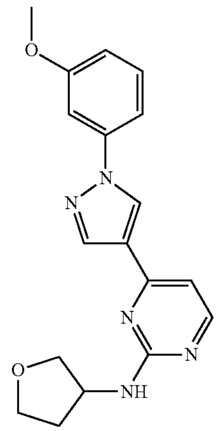 [SMILES: COc1cccc(-n2cc(-c3ccnc(NC4CCOC4)n3)cn2)c1] | NUCC-0077165 | 6 µM | | A |
| 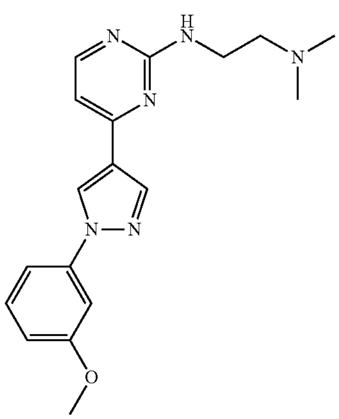 [SMILES: COc1cccc(-n2cc(-c3ccnc(NCCN(C)C)n3)cn2)c1] | NUCC-0077166 | 4 µM | | A |
| 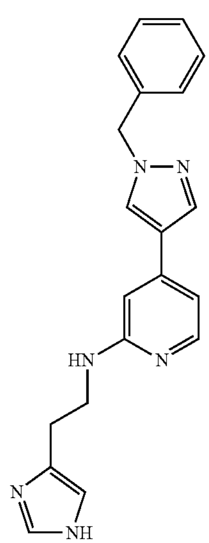 [SMILES: c1ccc(Cn2cc(-c3ccnc(NCCc4c[nH]cn4)c3)cn2)cc1] | NUCC-0077167 | 8 µM | 7.6 µM | C |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 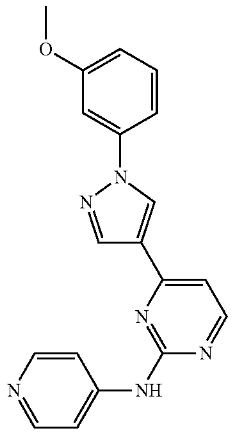 [SMILES: COc1cccc(-n2cc(-c3ccnc(Nc4ccncc4)n3)cn2)c1] | NUCC-0077168 | 19 µM | | A |
| 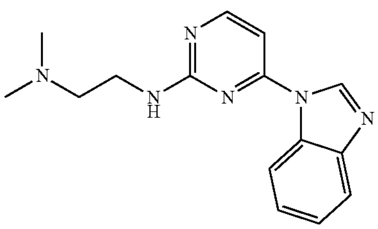 [SMILES: CN(C)CCNc1nccc(-n2cnc3ccccc32)n1] | NUCC-0125582 | 0.5 µM | 0.048 µM | B |
| 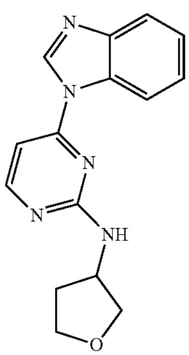 [SMILES: c1ccc2c(c1)ncn2-c1ccnc(NC2CCOC2)n1] | NUCC-0125583 | 0.04 µM | 0.0095 µM | B |
| 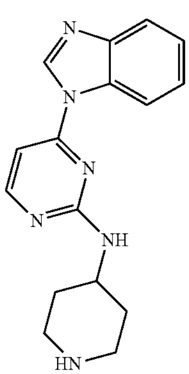 [SMILES: c1ccc2c(c1)ncn2-c1ccnc(NC2CCNCC2)n1] | NUCC-0125584 | 1.4 µM | | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 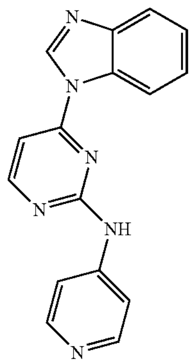 [SMILES: c1ccc2c(c1)ncn2-c1ccnc(Nc2ccncc2)n1] | NUCC-0125585 | 0.14 μM | | B |
| 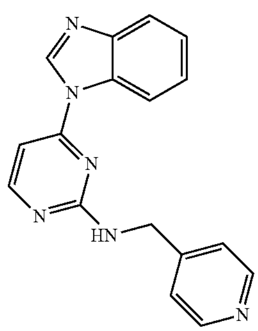 [SMILES: c1ccc2c(c1)ncn2-c1ccnc(NCc2ccncc2)n1] | NUCC-0125586 | 0.5 μM | | B |
| 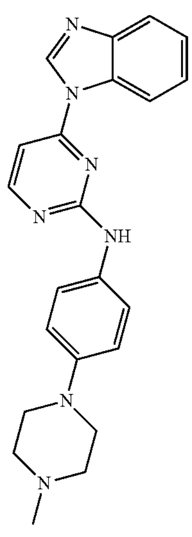 [SMILES: CN1CCN(c2ccc(Nc3nccc(-n4cnc5ccccc54)n3)cc2)CC1] | NUCC-0125587 | 0.5 μM | | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| (structure) | NUCC-0125588 | 0.2 μM | | B |
| (structure) | NUCC-0125589 | 13 μM | | A |
| (structure) | NUCC-0125590 | 6 μM | 0.78 μM | A |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 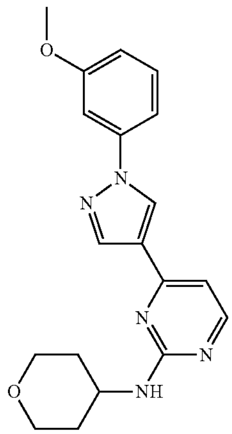 [SMILES: COc1cccc(-n2cc(-c3ccnc(NC4CCOCC4)n3)cn2)c1] | NUCC-0125591 | 21 μM | | A |
| 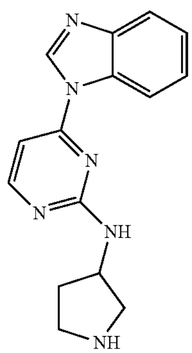 [SMILES: c1ccc2c(c1)ncn2-c1ccnc(NC2CCNC2)n1] | NUCC-0125592 | 0.15 μM | 0.040 μM | B |
| 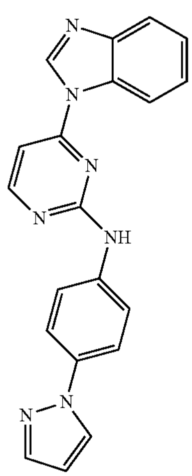 [SMILES: c1ccc2c(c1)ncn2-c1ccnc(Nc2ccc(-n3cccn3)cc2)n1] | NUCC-0125593 | 0.65 μM | 0.039 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 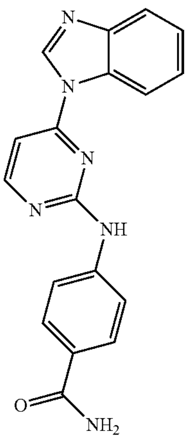 [SMILES: NC(=O)c1ccc(Nc2nccc(-n3cnc4ccccc43)n2)cc1] | NUCC-0125594 | 0.7 μM | 0.030 μM | B |
| 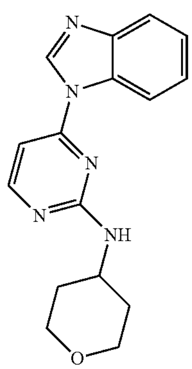 [SMILES: c1ccc2c(c1)ncn2-c1ccnc(NC2CCOCC2)n1] | NUCC-0125595 | 0.5 μM | 0.083 μM | B |
| 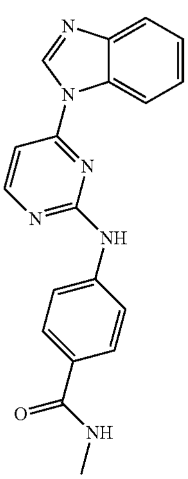 [SMILES: CNC(=O)c1ccc(Nc2nccc(-n3cnc4ccccc43)n2)cc1] | NUCC-0125596 | 0.2 μM | 0.034 μM | B |

TABLE 1-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 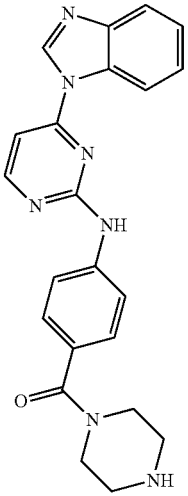 [SMILES: O=C(c1ccc(Nc2nccc(-n3cnc4ccccc43)n2)cc1)N1CCNCC1] | NUCC-0125597 | 6 μM | | B |
| 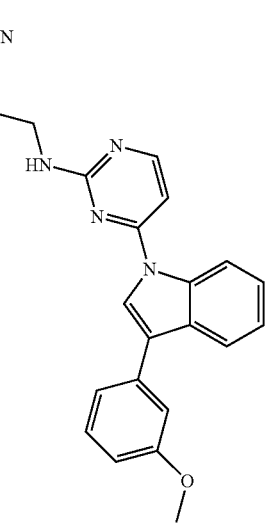 | NUCC-0125599 | 29 μM | 6.2 μM | D |
| 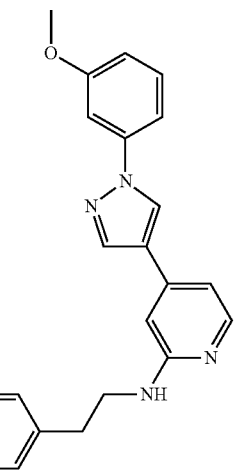 | NUCC-0125601 | 5 μM | 1.7 μM | D |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 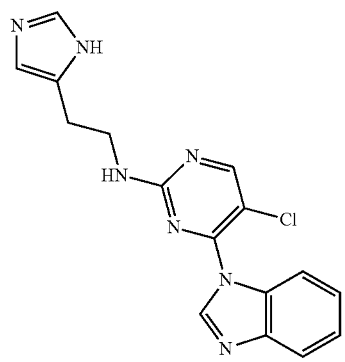 [SMILES: Clc1cnc(NCCc2cnc[nH]2)nc1-n1cnc2ccccc21] | NUCC-0175695 | 0.53 μM | 0.072 μM | B |
| 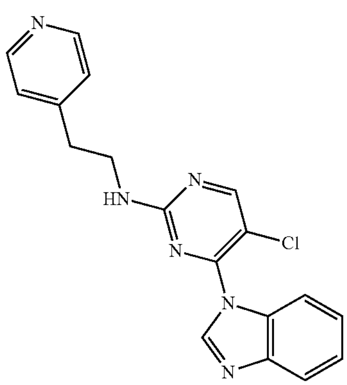 [SMILES: Clc1cnc(NCCc2ccncc2)nc1-n1cnc2ccccc21] | NUCC-0175697 | 0.02 μM | 0.0023 μM | B |
| 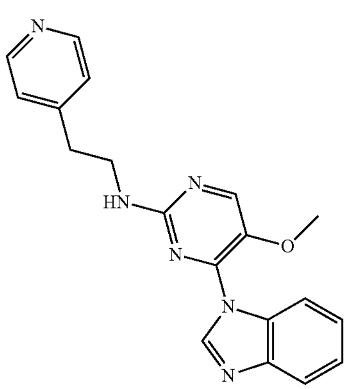 [SMILES: COc1cnc(NCCc2ccncc2)nc1-n1cnc2ccccc21] | NUCC-0175698 | 5.0 μM | 1.8 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 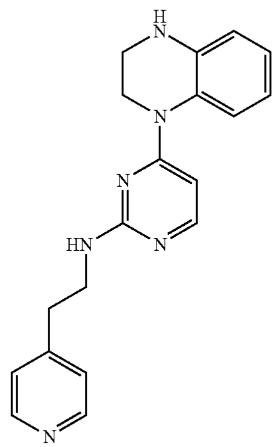 [SMILES: c1ccc2c(c1)NCCN2c1ccnc(NCCc2ccncc2)n1] | NUCC-0175722 | 1.2 μM | 0.25 μM | E |
| 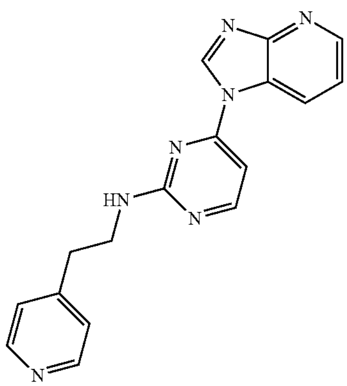 [SMILES: c1cnc2ncn(-c3ccnc(NCCc4ccncc4)n3)c2c1] | NUCC-0176138 | 8.5 μM | 6.0 μM | B |
| 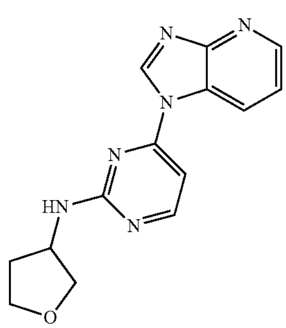 [SMILES: c1cnc2ncn(-c3ccnc(NC4CCOC4)n3)c2c1] | NUCC-0176142 | 13 μM | 5.3 μM | B |
| 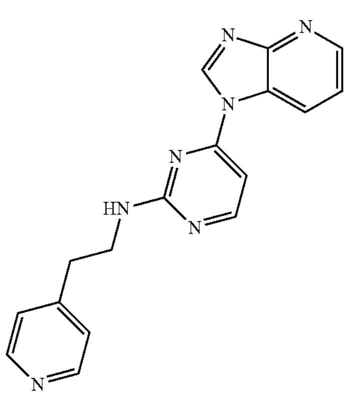 [SMILES: c1cnc2ncn(-c3ccnc(NCCc4ccncc4)n3)c2c1] | NUCC-0176143 | 4.3 μM | 1.1 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 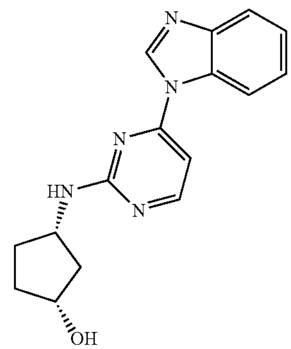 [SMILES: O[C@@H]1CC[C@H](Nc2nccc(-n3cnc4ccccc43)n2)C1] | NUCC-0176144 | 0.15 μM | 0.028 μM | B |
| 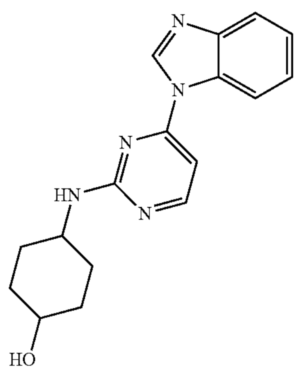 [SMILES: OC1CCC(Nc2nccc(-n3cnc4ccccc43)n2)CC1] | NUCC-0176145 | 0.40 μM | 0.052 μM | B |
| 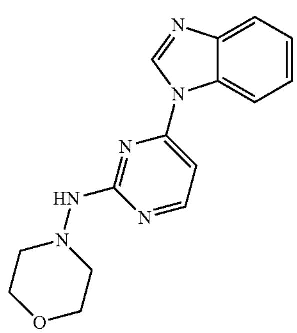 [SMILES: c1ccc2c(c1)ncn2-c1ccnc(NN2CCOCC2)n1] | NUCC-0176146 | 12 μM | 1.0 μM | B |
| 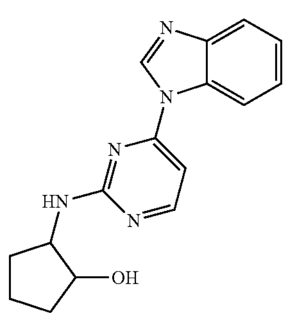 [SMILES: OC1CCCC1Nc1nccc(-n2cnc3ccccc32)n1] | NUCC-0176147 | 0.45 μM | 0.082 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 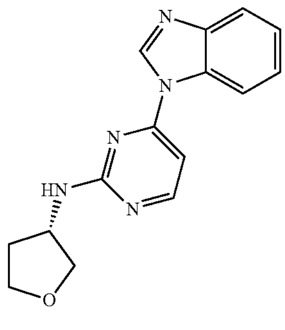 [SMILES: c1ccc2c(c1)ncn2-c1ccnc(N[C@H]2CCOC2)n1] | NUCC-0176148 | 0.19 μM | 0.046 μM | B |
| 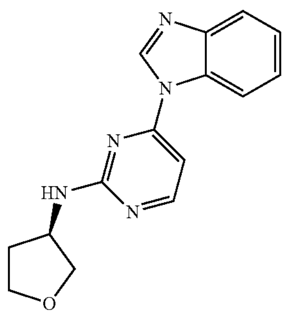 [SMILES: c1ccc2c(c1)ncn2-c1ccnc(N[C@@H]2CCOC2)n1] | NUCC-0176149 | 0.54 μM | 0.094 μM | B |
| 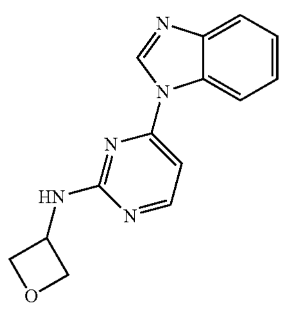 [SMILES: c1ccc2c(c1)ncn2-c1ccnc(NC2COC2)n1] | NUCC-0176150 | 0.42 μM | 0.090 μM | B |
| 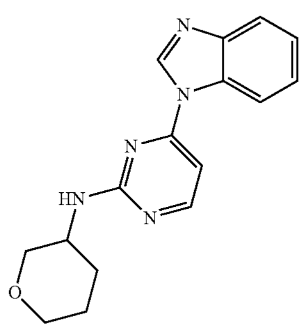 [SMILES: c1ccc2c(c1)ncn2-c1ccnc(NC2CCCOC2)n1] | NUCC-0176151 | 0.39 μM | 0.044 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 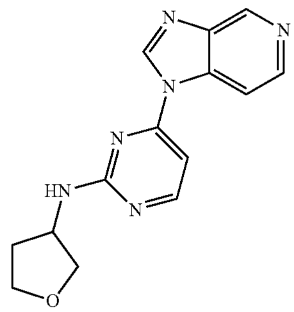 [SMILES: c1cc2c(cn1)ncn2-c1ccnc(NC2CCOC2)n1] | NUCC-0176152 | 1.6 μM | 1.3 μM | B |
| 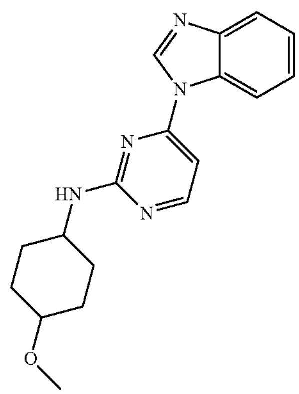 [SMILES: COC1CCC(Nc2nccc(-n3cnc4ccccc43)n2)CC1] | NUCC-0176153 | 0.48 μM | 0.081 μM | B |
| 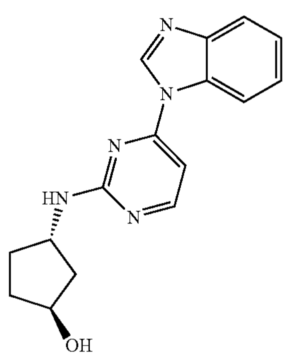 [SMILES: O[C@H]1CC[C@H](Nc2nccc(-n3cnc4ccccc43)n2)C1] | NUCC-0176163 | 0.20 μM | 0.041 μM | B |
| 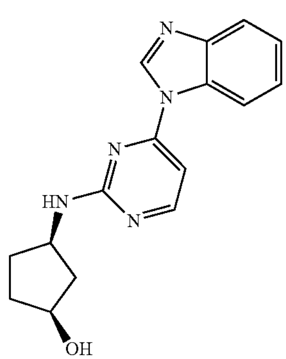 [SMILES: O[C@H]1CC[C@@H](Nc2nccc(-n3cnc4ccccc43)n2)C1] | NUCC-0176164 | 0.10 μM | 0.026 μM | B |

TABLE 1-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 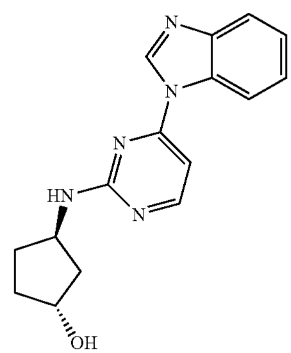 [SMILES: O[C@@H]1CC[C@@H](Nc2nccc(-n3cnc4ccccc43)n2)C1] | NUCC-0176165 | 0.34 µM | 0.061 µM | B |
| 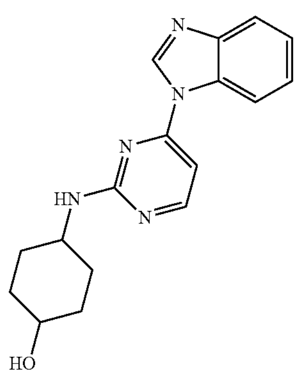 [SMILES: OC1CCC(Nc2nccc(-n3cnc4ccccc43)n2)CC1] | NUCC-0176166 | 0.39 µM | 0.063 µM | B |
| 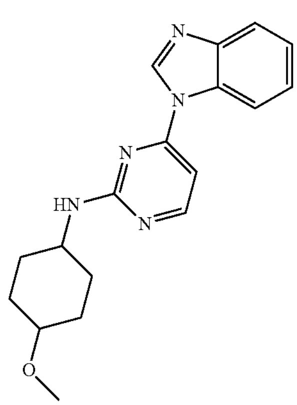 [SMILES: COC1CCC(Nc2nccc(-n3cnc4ccccc43)n2)CC1] | NUCC-0176167 | 0.30 µM | 0.060 µM | B |

TABLE 2

| Structure | Molecule Name | Mnk1 IC$_{50}$ | Mnk2 IC$_{50}$ | Synthetic Route |
|---|---|---|---|---|
| 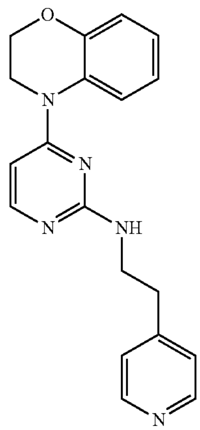 [SMILES: c1ccc2c(c1)OCCN2c1ccnc(NCCc2ccncc2)n1] | NUCC-0176230 | 5.1 µM | 3.5 µM | B |
| 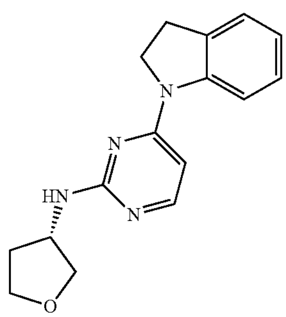 [SMILES: c1ccc2c(c1)CCN2c1ccnc(N[C@H]2CCOC2)n1] | NUCC-0176231 | 1.1 µM | 0.38 µM | B |
| 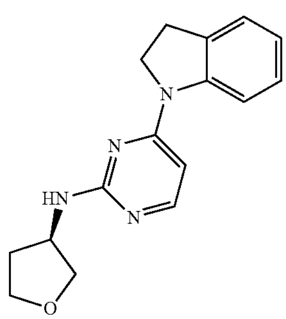 [SMILES: c1ccc2c(c1)CCN2c1ccnc(N[C@@H]2CCOC2)n1] | NUCC-0176232 | 4.6 µM | 2.3 µM | B |
| 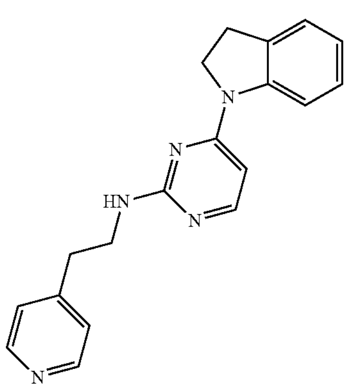 [SMILES: c1ccc2c(c1)CCN2c1ccnc(NCCc2ccncc2)n1] | NUCC-0176233 | 8.5 µM | 4.7 µM | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 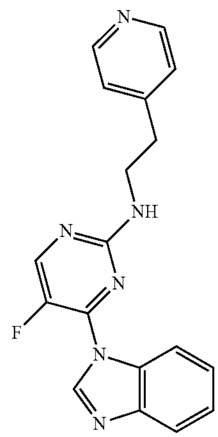 [SMILES: Fc1cnc(NCCc2ccncc2)nc1-n1cnc2ccccc21] | NUCC-0176281 | 0.33 μM | 0.049 μM | B |
| 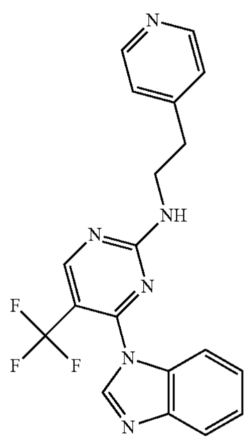 [SMILES: FC(F)(F)c1cnc(NCCc2ccncc2)nc1-n1cnc2ccccc21] | NUCC-0176282 | 0.093 μM | 0.028 μM | B |
| 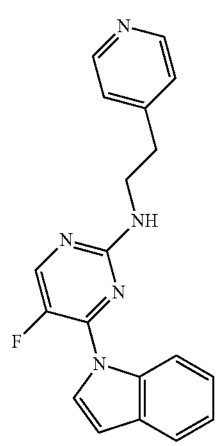 [SMILES: Fc1cnc(NCCc2ccncc2)nc1-n1ccc2ccccc21] | NUCC-0176283 | 8.7 μM | 10 μM | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 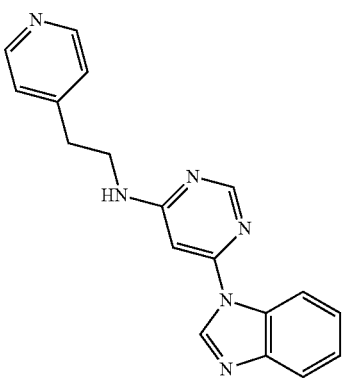 [SMILES: c1ccc2c(c1)ncn2-c1cc(NCCc2ccncc2)ncn1] | NUCC-0176284 | 2.6 μM | 1.2 μM | B |
| 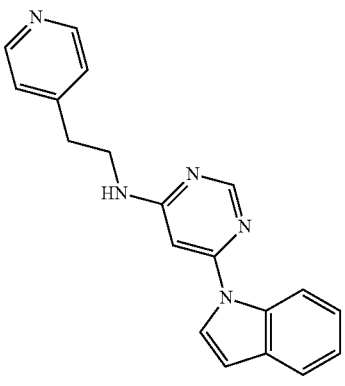 [SMILES: c1ccc2c(c1)ccn2-c1cc(NCCc2ccncc2)ncn1] | NUCC-0176285 | 4.7 μM | 6.0 μM | B |
| 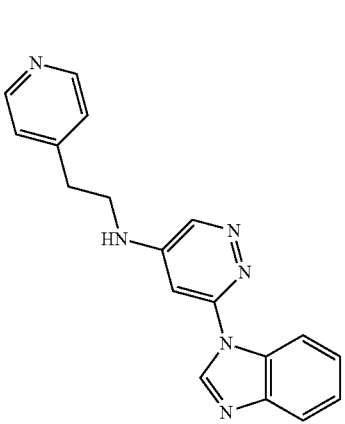 [SMILES: c1ccc2c(c1)ncn2-c1cc(NCCc2ccncc2)cnn1] | NUCC-0176338 | no activity | no activity | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 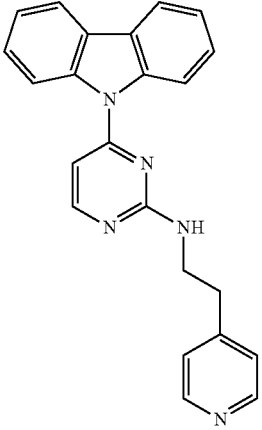 [SMILES: c1ccc2c(c1)c1ccccc1n2-c1ccnc(NCCc2ccncc2)n1] | NUCC-0176339 | 11 μM | 10 μM | B |
| 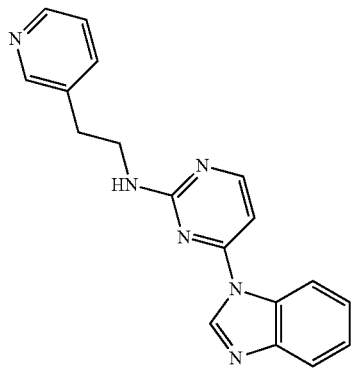 [SMILES: c1cncc(CCNc2nccc(-n3cnc4ccccc43)n2)c1] | NUCC-0176340 | 0.55 μM | 0.069 μM | B |
| 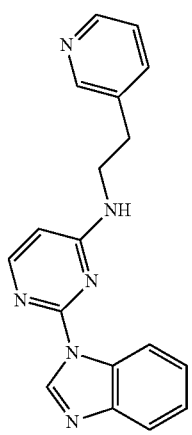 [SMILES: c1cncc(CCNc2ccnc(-n3cnc4ccccc43)n2)c1] | NUCC-0176341 | 0.21 μM | 0.026 μM | B |
| 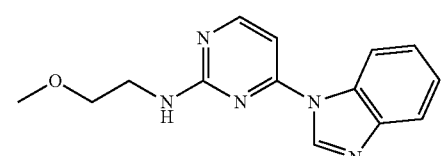 | NUCC-0176342 | 1.6 μM | 0.20 μM | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 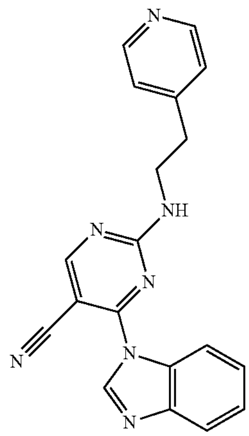 [SMILES: N#Cc1cnc(NCCc2ccncc2)nc1-n1cnc2ccccc21] | NUCC-0176343 | 0.0065 µM | 0.0032 µM | B |
| 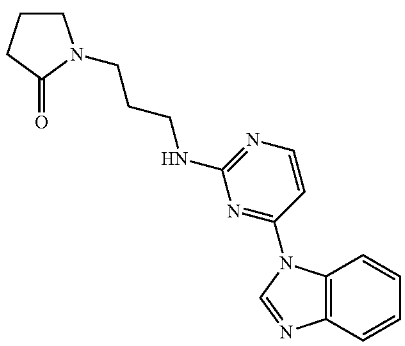 [SMILES: O=C1CCCN1CCCNc1nccc(-n2cnc3ccccc32)n1] | NUCC-0176344 | 7.2 µM | 0.78 µM | B |
| 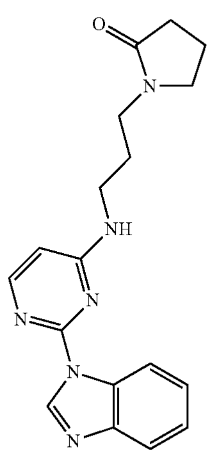 [SMILES: O=C1CCCN1CCCNc1ccnc(-n2cnc3ccccc32)n1] | NUCC-0176345 | 10 µM | 2.6 µM | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 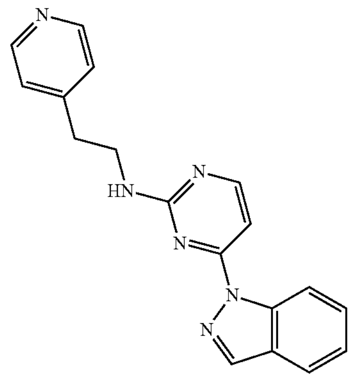 [SMILES: c1ccc2c(c1)cnn2-c1ccnc(NCCc2ccncc2)n1] | NUCC-0176346 | 5.4 μM | 4.7 μM | B |
| 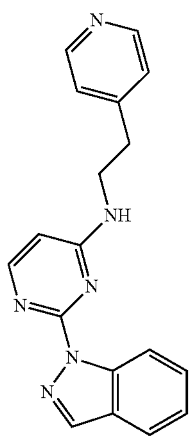 [SMILES: c1ccc2c(c1)cnn2-c1nccc(NCCc2ccncc2)n1] | NUCC-0176347 | 8.1 μM | 5.6 μM | B |
| 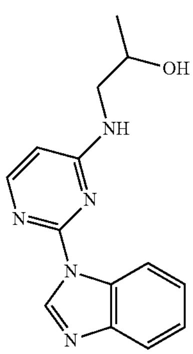 [SMILES: CC(O)CNc1ccnc(-n2cnc3ccccc32)n1] | NUCC-0176348 | 0.71 μM | 0.13 μM | B |
| 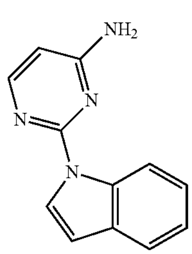 [SMILES: Nc1ccnc(-n2ccc3ccccc32)n1] | NUCC-0176349 | 4.1 μM | 1.4 μM | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 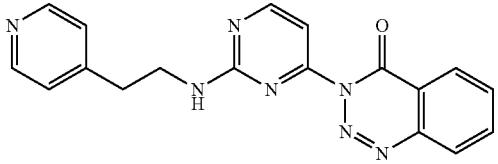 [SMILES: O=c1c2ccccc2nnn1-c1ccnc(NCCc2ccncc2)n1] | NUCC-0176350 | no activity | no activity | B |
| 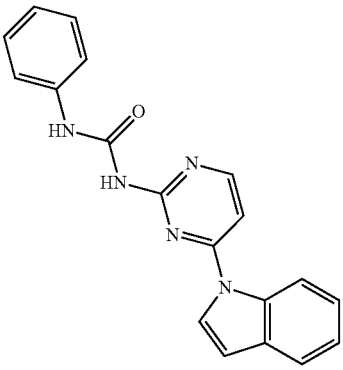 [SMILES: O=C(Nc1ccccc1)Nc1nccc(-n2ccc3ccccc32)n1] | NUCC-0176351 | no activity | no activity | B |
| 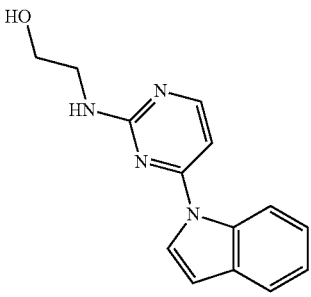 [SMILES: OCCNc1nccc(-n2ccc3ccccc32)n1] | NUCC-0176352 | 0.65 µM | 0.17 µM | B |
| 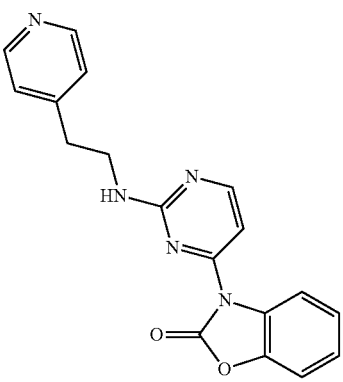 [SMILES: O=c1oc2ccccc2n1-c1ccnc(NCCc2ccncc2)n1] | NUCC-0176353 | 9.5 µM | 6.8 µM | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 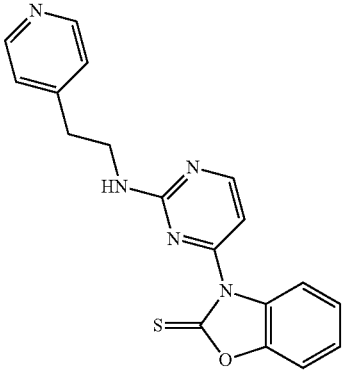 [SMILES: S=c1oc2ccccc2n1-c1ccnc(NCCc2ccncc2)n1] | NUCC-0176354 | 10 μM | 4.9 μM | B |
| 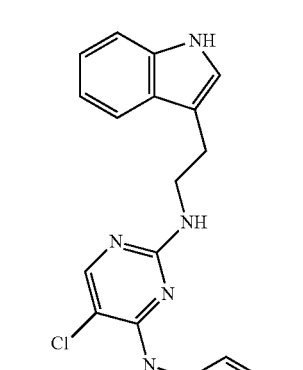 | NUCC-0176355 | 13 μM | 2.4 μM | B |
| 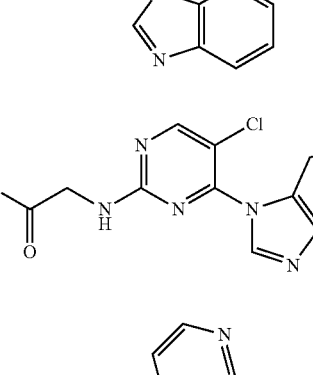 | NUCC-0176356 | 11 μM | 1.4 μM | B |
| 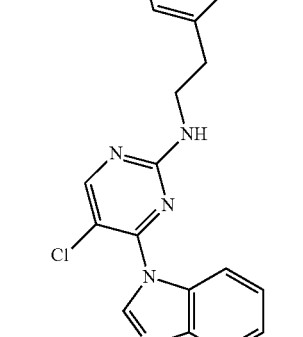 | NUCC-0176357 | 2.3 μM | 0.25 μM | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 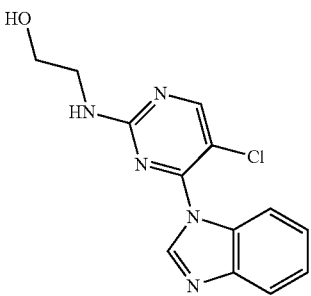 [SMILES: OCCNc1ncc(Cl)c(-n2cnc3ccccc32)n1] | NUCC-0176358 | 0.45 μM | 0.13 μM | B |
| 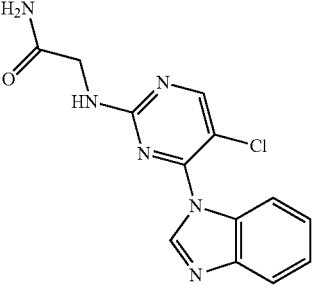 | NUCC-0176359 | 1.5 μM | 0.32 μM | B |
| 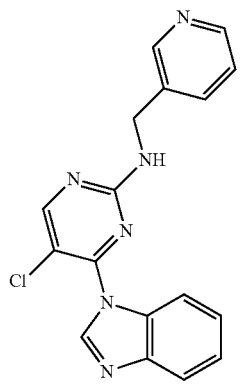 [SMILES: Clc1cnc(NCc2cccnc2)nc1-n1cnc2ccccc21] | NUCC-0176360 | 4.5 μM | 1.0 μM | B |
| 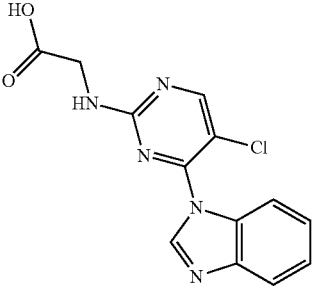 [SMILES: O=C(O)CNc1ncc(Cl)c(-n2cnc3ccccc32)n1] | NUCC-0176361 | no activity | no activity | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 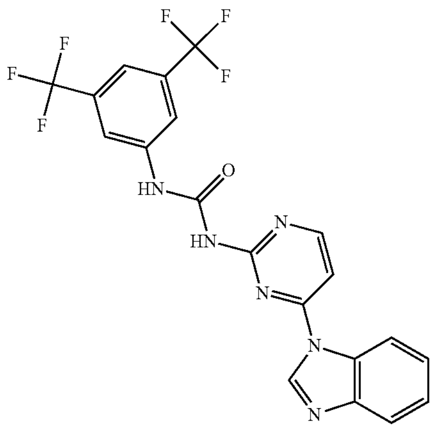 [SMILES: O=C(Nc1cc(C(F)(F)F)cc(C(F)(F)F)c1)Nc1nccc(-n2cnc3ccccc32)n1] | NUCC-0176362 | no activity | no activity | B |
| 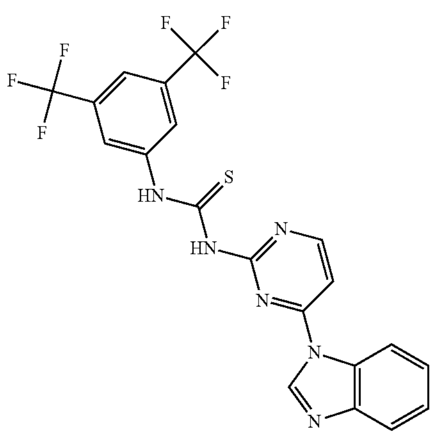 [SMILES: FC(F)(F)c1cc(NC(=S)Nc2nccc(-n3cnc4ccccc43)n2)cc(C(F)(F)F)c1] | NUCC-0176363 | no activity | no activity | B |
| 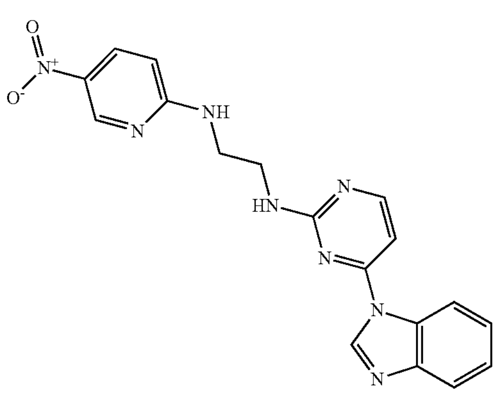 [SMILES: O=[N+]([O-])c1ccc(NCCNc2nccc(-n3cnc4ccccc43)n2)nc1] | NUCC-0176365 | 7.4 µM | 2.1 µM | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 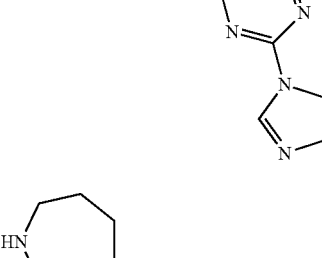 | NUCC-0176366 | 8.5 μM | 2.5 μM | B |
| 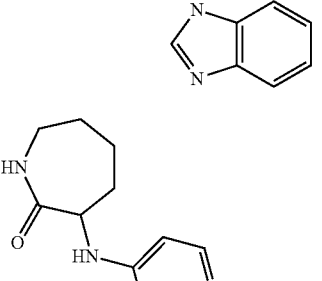 | NUCC-0176367 | 2.6 μM | 0.5 μM | B |
| 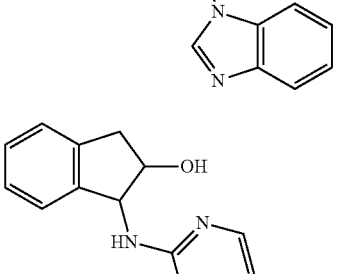 | NUCC-0176368 | 11 μM | 5.2 μM | B |
| 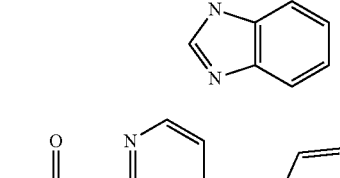 | NUCC-0176369 | no activity | no activity | B |
| 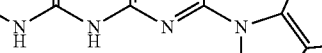 | NUCC-0196222 | >10 | 2.2 | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 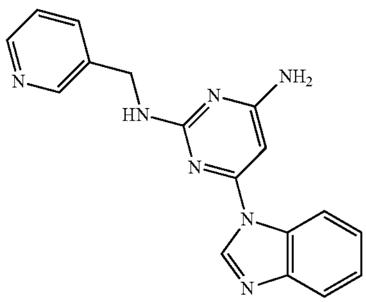 [SMILES: Nc1cc(-n2cnc3ccccc32)nc(NCc2cccnc2)n1] | NUCC-0196223 | >10 | 1.8 | B |
| 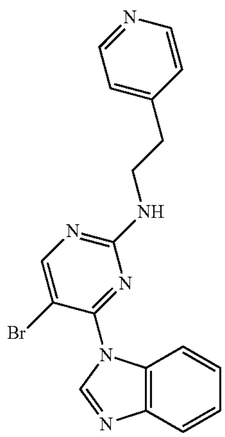 | NUCC-0196228 | 0.55 | 0.069 | B |
| 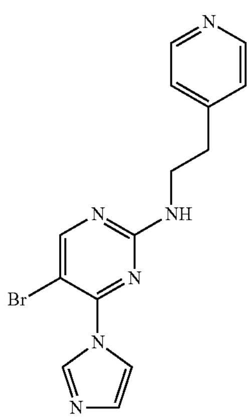 [SMILES: Brc1cnc(NCCc2ccncc2)nc1-n1ccnc1] | NUCC-0196229 | 0.48 | 1.2 | B |
| 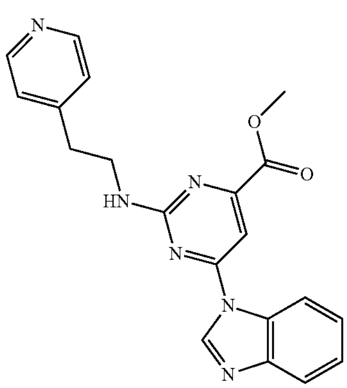 [SMILES: COC(=O)c1cc(-n2cnc3ccccc32)nc(NCCc2ccncc2)n1] | NUCC-0196230 | >10 | >10 | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 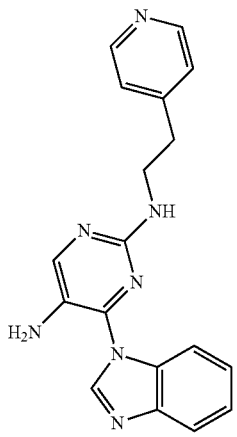 [SMILES: Nc1cnc(NCCc2ccncc2)nc1-n1cnc2ccccc21] | NUCC-0196231 | >10 | >10 | B |
| 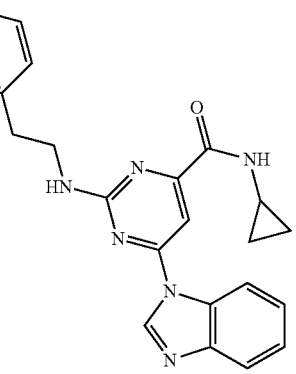 | NUCC-0196234 | >10 | 5.4 | B |
| 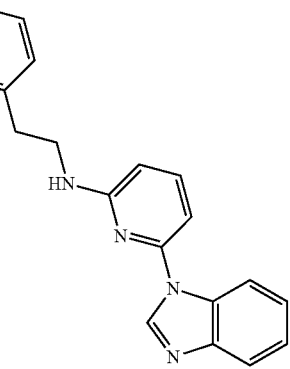 | NUCC-0196235 | 0.1 | 0.01 | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 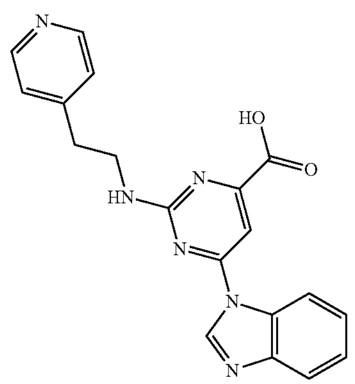 [SMILES: O=C(O)c1cc(-n2cnc3ccccc32)nc(NCCc2ccncc2)n1] | NUCC-0196239 | >10 | 6.9 | B |
| 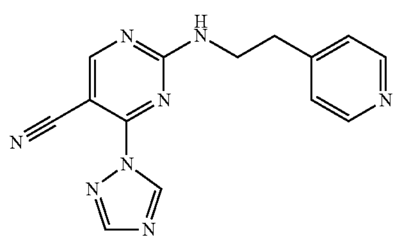 [SMILES: N#Cc1cnc(NCCc2ccncc2)nc1-n1cncn1] | NUCC-0196250 | >10 | >10 | B |
| 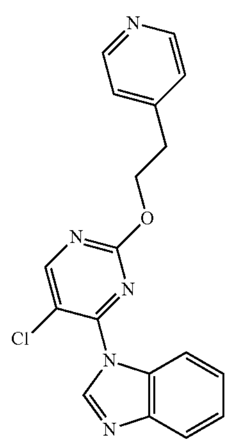 [SMILES: Clc1cnc(OCCc2ccncc2)nc1-n1cnc2ccccc21] | NUCC-0196254 | 0.054 | 0.0096 | B |
| 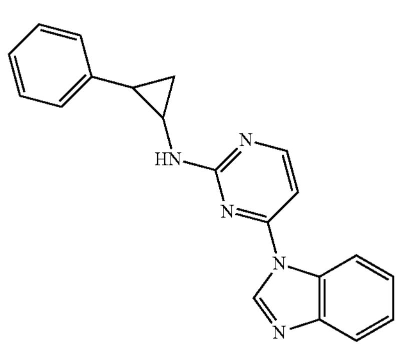 [SMILES: c1ccc(C2CC2Nc2nccc(-n3cnc4ccccc43)n2)cc1] | NUCC-0196255 | >10 | 0.92 | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 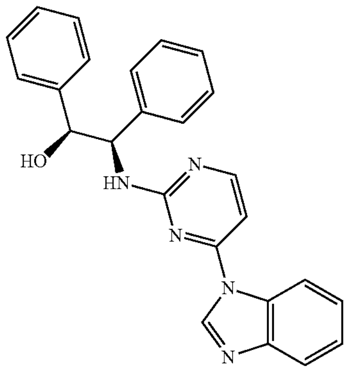 [SMILES: O[C@@H](c1ccccc1)[C@H](Nc1nccc(-n2cnc3ccccc32)n1)c1ccccc1] | NUCC-0196256 | 7.3 | 3.8 | B |
| 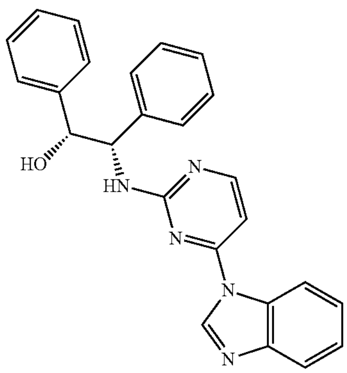 [SMILES: O[C@H](c1ccccc1)[C@@H](Nc1nccc(-n2cnc3ccccc32)n1)c1ccccc1] | NUCC-0196257 | 1.3 | 0.31 | B |
| 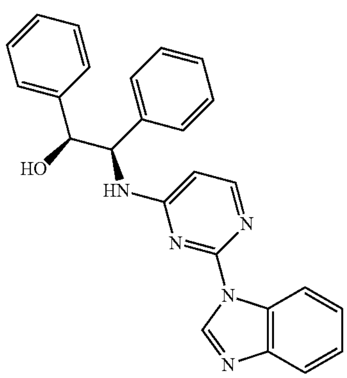 | NUCC-0196258 | >10 | 7 | B |
| 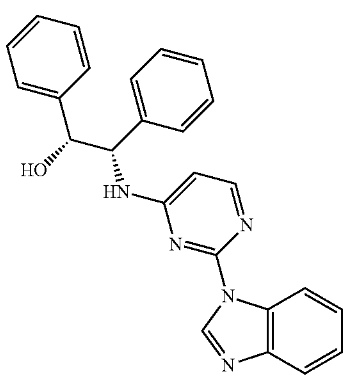 [SMILES: O[C@H](c1ccccc1)[C@@H](Nc1ccnc(-n2cnc3ccccc32)n1)c1ccccc1] | NUCC-0196259 | 5.6 | 0.32 | B |

TABLE 2-continued
Mnk1 and Mnk2 Inhibition.
| Structure | Molecule Name | Mnk1 IC$_{50}$ | Mnk2 IC$_{50}$ | Synthetic Route |
|---|---|---|---|---|
| 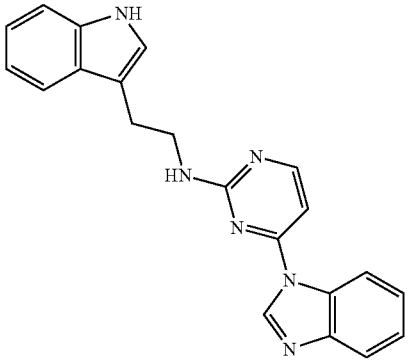 [SMILES: c1ccc2c(c1)ncn2-c1ccnc(NCCc2c[nH]c3ccccc23)n1] | NUCC-0196260 | 0.5 | 0.09 | B |
| 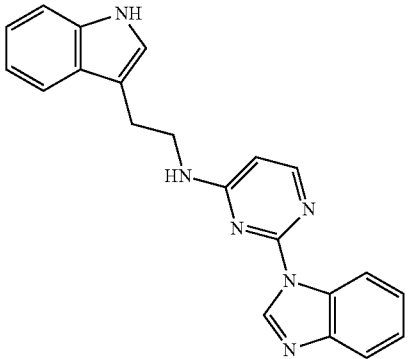 [SMILES: c1ccc2c(c1)ncn2-c1nccc(NCCc2c[nH]c3ccccc23)n1] | NUCC-0196261 | 0.92 | 0.11 | B |
| 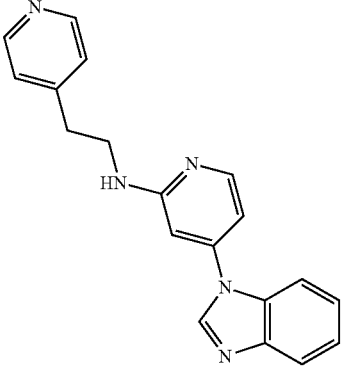 [SMILES: c1ccc2c(c1)ncn2-c1ccnc(NCCc2ccncc2)c1] | NUCC-0196262 | 1.3 | 1.2 | B |
| 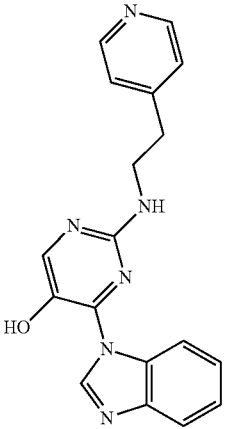 [SMILES: Oc1cnc(NCCc2ccncc2)nc1-n1cnc2ccccc21] | NUCC-0196263 | >10 | >10 | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 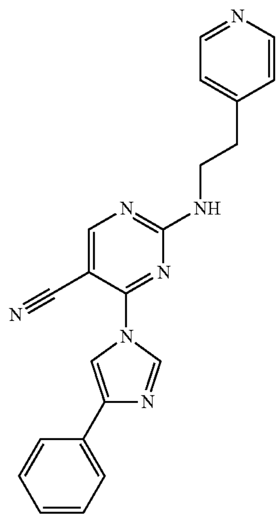 [SMILES: N#Cc1cnc(NCCc2ccncc2)nc1-n1cnc(-c2ccccc2)c1] | NUCC-0196264 | 0.096 | 0.057 | B |
| 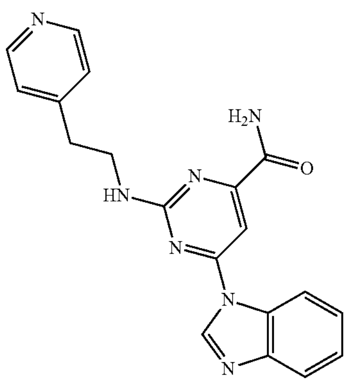 [SMILES: NC(=O)c1cc(-n2cnc3ccccc32)nc(NCCc2ccncc2)n1] | NUCC-0196265 | 1.6 | 0.89 | B |
| 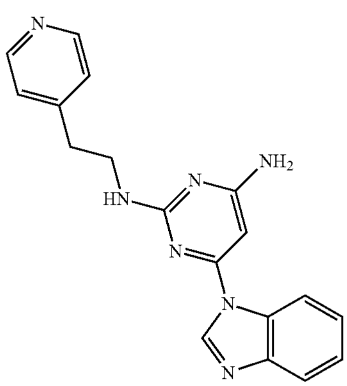 [SMILES: Nc1cc(-n2cnc3ccccc32)nc(NCCc2ccncc2)n1] | NUCC-0196307 | 0.87 | 0.17 | B |
| 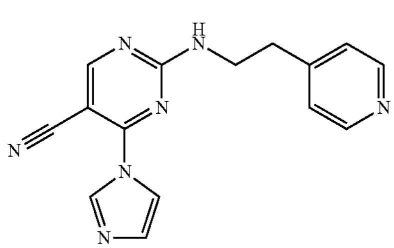 [SMILES: N#Cc1cnc(NCCc2ccncc2)nc1-n1ccnc1] | NUCC-0196308 | 2.1 | 6.9 | B |

TABLE 2-continued

Mnk1 and Mnk2 Inhibition.

| Structure | Molecule Name | Mnk1 IC$_{50}$ | Mnk2 IC$_{50}$ | Synthetic Route |
|---|---|---|---|---|
| 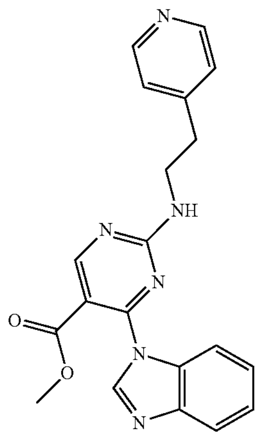 [SMILES: COC(=O)c1cnc(NCCc2ccncc2)nc1-n1cnc2ccccc21] | NUCC-0196309 | >10 | >10 | B |
| 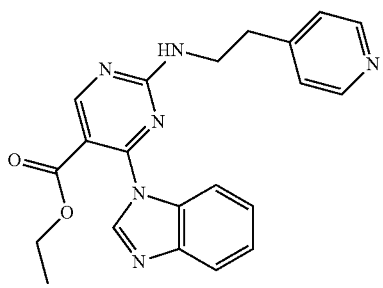 [SMILES: CCOC(=O)c1cnc(NCCc2ccncc2)nc1-n1cnc2ccccc21] | NUCC-0196310 | 2.1 | 5.4 | B |

TABLE 3

Cell Inhibition of Mnk1 and Cell Viability Assays.

| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| NUCC-0054131 | 4.2 μM | 0.80 μM | | |

TABLE 3-continued
Cell Inhibition of Mnk1 and Cell Viability Assays.
| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| 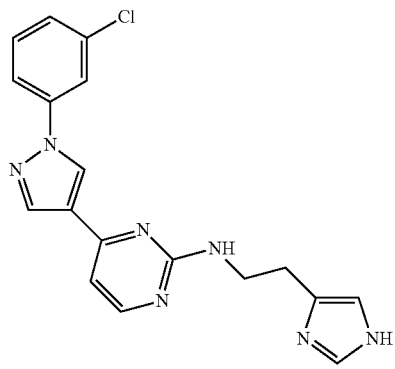 NUCC-0054135 | 0.081 μM | 0.066 μM | 3.4 μM | 0.24 μM |
| 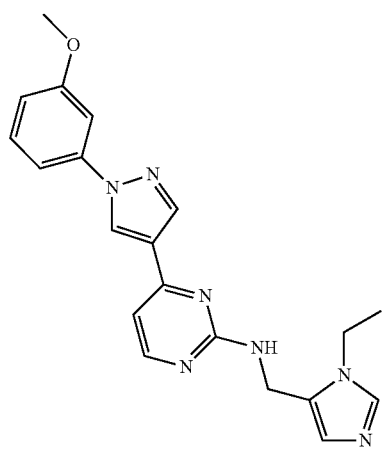 NUCC-0054136 | 0.14 μM | 0.10 μM | 10 μM | 4.5 μM |
| 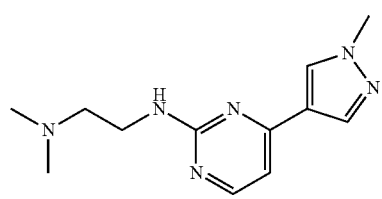 NUCC-0060898 | 0.042 μM | 0.035 μM | 13 μM | 0.19 μM |

TABLE 3-continued
Cell Inhibition of Mnk1 and Cell Viability Assays.
| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| 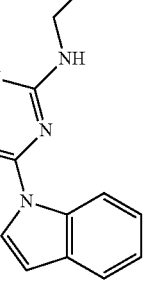 NUCC-0060954 | 0.014 μM | 0.010 μM | 2.6 μM | 0.41 μM |
| 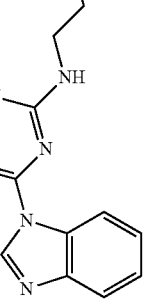 NUCC-0060957 | 0.062 μM | 0.020 μM | 5.3 μM | 0.12 μM |
| 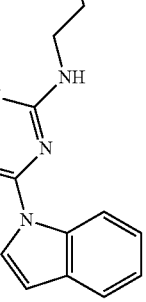 NUCC-0060958 | 0.23 μM | 0.047 μM | | |

TABLE 3-continued
Cell Inhibition of Mnk1 and Cell Viability Assays.
| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| 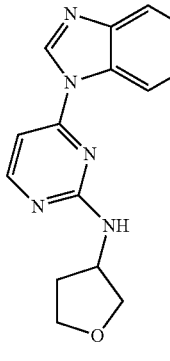 NUCC-0125583 | 0.0055 µM | 0.007 µM | >10 µM | 0.62 µM |
| 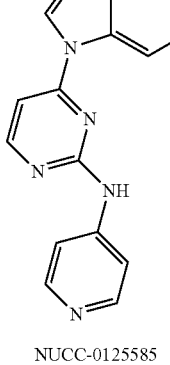 NUCC-0125585 | 0.051 µM | 0.040 µM | 10 µM | 0.31 µM |
| 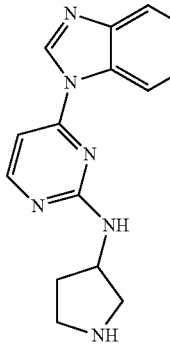 NUCC-0125592 | 1.1 µM | 0.069 µM | >10 µM | 0.08 µM |

TABLE 3-continued

Cell Inhibition of Mnk1 and Cell Viability Assays.

| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| NUCC-0175695 | 0.63 µM | 0.37 µM | >10 µM | 1.0 µM |
| NUCC-075697 | 0.052 µM | 0.039 µM | 7 µM | 0.35 µM |
| NUCC-0176144 | 0.078 µM | 0.078 µM | 5.7 µM | 0.17 µM |

TABLE 3-continued

Cell Inhibition of Mnk1 and Cell Viability Assays.

| Structure | U937 pEIF4E IC$_{50}$ | MV4-11 pEIF4E IC$_{50}$ | U937 viability EC$_{50}$ | MV4-11 viability EC$_{50}$ |
| --- | --- | --- | --- | --- |
| NUCC-0176148 | 0.10 μM | 0.037 μM | >10 μM | 0.44 μM |
| NUCC-0176163 | 0.075 μM | 0.074 μM | 8.1 μM | 0.22 μM |
| NUCC-0176164 | 0.062 μM | 0.036 μM | >10 μM | 0.18 μM |

TABLE 4

Cell Inhibition of Mnk1 and Cell Viability Assays.

| Structure | U937 pEIF4E IC$_{50}$ | MV4-11 pEIF4E IC$_{50}$ | U937 viability EC$_{50}$ | MV4-11 viability EC$_{50}$ |
|---|---|---|---|---|
| 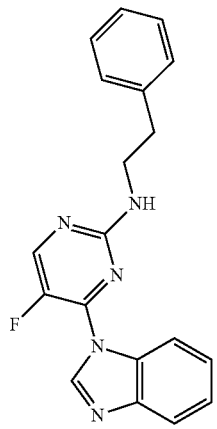 NUCC-0176281 | 0.081 μM | 0.066 μM | 3.4 μM | 0.24 μM |
| 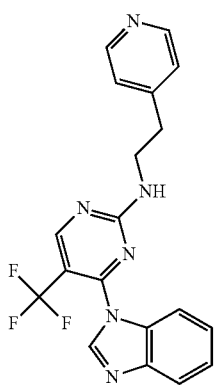 NUCC-0176282 | 0.14 μM | 0.10 μM | 10 μM | 4.5 μM |
| 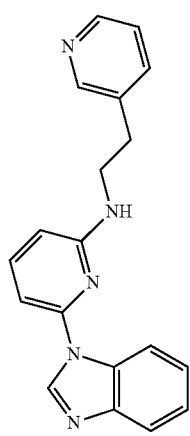 NUCC-0176341 | 0.042 μM | 0.035 μM | 13 μM | 0.19 μM |
| 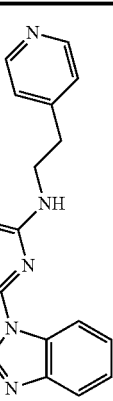 NUCC-0176343 | 0.014 μM | 0.010 μM | 2.6 μM | 0.41 μM |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula selected from Formula II and III:

II

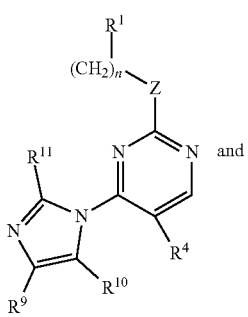

III

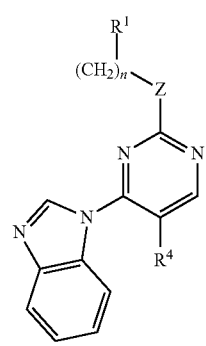

wherein:

Z is NH or O;

n=0, 1, 2, or 3;

R¹ is hydrogen, alkyl, alkoxyl, hydroxyl, hydroxyalkyl, carboxyl, carboxyalkylester, cycloalkyl optionally substituted at one or more positions with hydroxyl or alkoxyl, amino optionally substituted with alkyl, amido optionally substituted with phenyl or substituted phenyl, thioamido, phenyl optionally substituted at one or more positions with halo or amido, pyridinyl, pyrrolidinyl, tetrahydropyranyl, tetrahydrofuranyl, oxetanyl, pyrrolidonyl, piperidinyl, piperazinyl optionally substituted with alkyl, morpholinyl, imidazolyl optionally substituted at one or more positions with alkyl, pyrazolyl, benzyamidyl, N-methylbenzamid-4-yl, benzoyl, benzoylpiperazine, N-phenylformamidyl, indolyl, or R¹ has a structure selected from

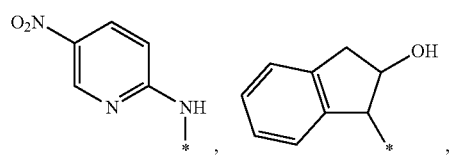

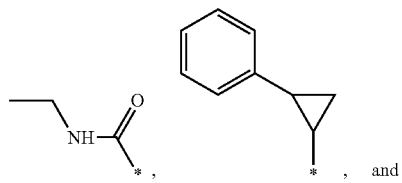

-continued

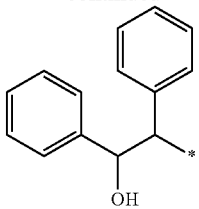

$R_4$ is hydrogen, alkyl, haloalkyl, halo, alkoxyl, cyano, amino, hydroxyl, carboxyl, or carboxy alkyl ester; and $R^9$, $R^{10}$, and $R^{11}$ are the same or different and are hydrogen, alkyl, or phenyl, wherein at least one of $R^9$ and $R^{10}$ is phenyl.

2. The compound of claim 1, having a formula selected from:

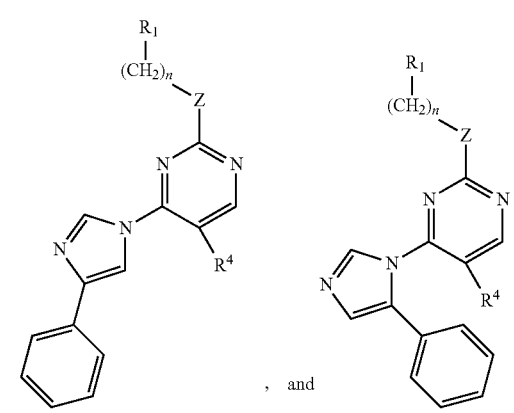

3. The compound of claim 2, wherein $R^4$ is halo or cyano.

4. The compound of claim 2, wherein $R^1$ is pyridin-3-yl or pyridin-4-yl.

5. A compound having a formula:

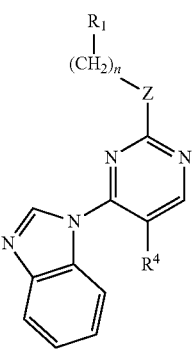

wherein:

Z is NH or O;

n=0, 1, 2, or 3;

R¹ is hydrogen, alkyl, alkoxyl, hydroxyl, hydroxyalkyl, carboxyl, carboxyalkylester, cycloalkyl optionally substituted at one or more positions with hydroxyl or alkoxyl, amino optionally substituted with alkyl, amido optionally substituted with phenyl or substituted phenyl, thioamido, phenyl optionally substituted at one or more positions with halo or amido, pyridinyl, pyrrolidinyl, tetrahydropyranyl, tetrahydrofuranyl, oxetanyl, pyrrolidonyl, piperidinyl, piperazinyl optionally substituted with alkyl, morpholinyl, imidazolyl optionally substituted at one or more positions with alkyl, pyrazolyl, benzyamidyl, N-methylbenzamid-4-yl, benzoyl, benzoylpiperazine, N-phenylformamidyl, indolyl, or $R^1$ has a structure selected from

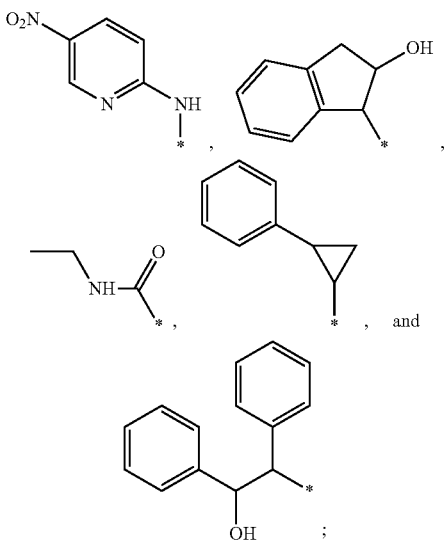

and
$R_4$ is hydrogen, alkyl, haloalkyl, halo, alkoxyl, cyano, amino, hydroxyl, carboxyl, or carboxy alkyl ester.

6. The compound of claim 5 wherein $R^4$ is halo or cyano.
7. The compound of claim 5 wherein $R^1$ is pyridin-3-yl or pyridin-4-yl.
8. A compound having a formula:

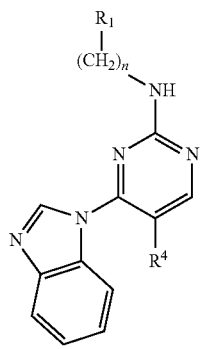

wherein:
n=0, 1, 2, or 3;
$R^1$ is hydrogen, alkyl, alkoxyl, hydroxyl, hydroxyalkyl, carboxyl, carboxyalkylester, cycloalkyl optionally substituted at one or more positions with hydroxyl or alkoxyl, amino optionally substituted with alkyl, amido optionally substituted with phenyl or substituted phenyl, thioamido, phenyl optionally substituted at one or more positions with halo or amido, pyridinyl, pyrrolidinyl, tetrahydropyranyl, tetrahydrofuranyl, oxetanyl, pyrrolidonyl, piperidinyl, piperazinyl optionally substituted with alkyl, morpholinyl, imidazolyl optionally substituted at one or more positions with alkyl, pyrazolyl, benzyamidyl, N-methylbenzamid-4-yl, benzoyl, benzoylpiperazine, N-phenylformamidyl, indolyl, or $R^1$ has a structure selected from

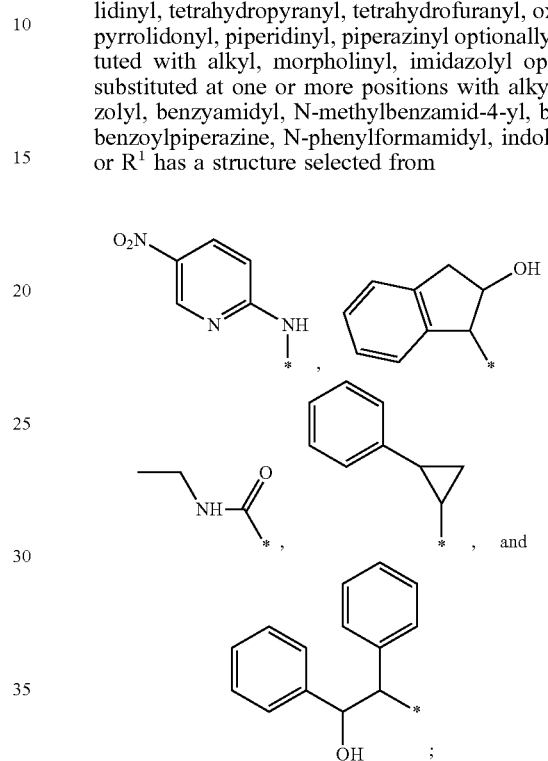

$R_4$ is hydrogen, alkyl, haloalkyl, halo, alkoxyl, cyano, amino, hydroxyl, carboxyl, or carboxy alkyl ester.

9. The compound of claim 8, wherein $R^4$ is halo or cyano.
10. The compound of claim 8 wherein $R^1$ is pyridin-3-yl or pyridin-4-yl.
11. A pharmaceutical composition comprising an effective amount of the compound of claim 1 together with a carrier, excipient, or diluent.
12. A pharmaceutical composition comprising an effective amount of the compound of claim 5 together with a carrier, excipient, or diluent.
13. A pharmaceutical composition comprising an effective amount of the compound of claim 8 together with a carrier, excipient, or diluent.

* * * * *